(12) United States Patent
Porteus et al.

(10) Patent No.: US 11,903,969 B2
(45) Date of Patent: Feb. 20, 2024

(54) GENOME EDITING OF GRAFT-DERIVED T-CELLS FOR POST-TRANSPLANT IMMUNOTHERAPY

(71) Applicant: The Board of Trustees of the Leland Stanford Junior University, Stanford, CA (US)

(72) Inventors: Matthew H. Porteus, Stanford, CA (US); Alice Bertaina, Stanford, CA (US); Volker Andreas Wiebking, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 491 days.

(21) Appl. No.: 17/098,258

(22) Filed: Nov. 13, 2020

(65) Prior Publication Data

US 2021/0177899 A1 Jun. 17, 2021

Related U.S. Application Data

(60) Provisional application No. 62/934,994, filed on Nov. 13, 2019.

(51) Int. Cl.
| | |
|---|---|
| *A61K 35/17* | (2015.01) |
| *C12N 15/11* | (2006.01) |
| *C12N 9/22* | (2006.01) |
| *C07K 16/28* | (2006.01) |
| *C12N 5/0783* | (2010.01) |
| *C12N 15/90* | (2006.01) |
| *C12N 15/86* | (2006.01) |
| *C12N 7/00* | (2006.01) |
| *C07K 14/705* | (2006.01) |
| *A61P 35/02* | (2006.01) |
| *A61K 38/00* | (2006.01) |
| *A61K 39/00* | (2006.01) |
| *A61K 9/00* | (2006.01) |
| *C07K 14/725* | (2006.01) |

(52) U.S. Cl.
CPC ............ *A61K 35/17* (2013.01); *A61K 9/0019* (2013.01); *A61P 35/02* (2018.01); *C07K 14/7051* (2013.01); *C07K 14/70521* (2013.01); *C07K 16/2803* (2013.01); *C12N 5/0636* (2013.01); *C12N 7/00* (2013.01); *C12N 9/22* (2013.01); *C12N 15/11* (2013.01); *C12N 15/86* (2013.01); *C12N 15/907* (2013.01); *A61K 38/00* (2013.01); *A61K 2039/505* (2013.01); *A61K 2039/5154* (2013.01); *A61K 2039/5156* (2013.01); *A61K 2039/5158* (2013.01); *A61K 2039/54* (2013.01); *A61K 2039/55* (2013.01); *C07K 2317/76* (2013.01); *C07K 2319/30* (2013.01); *C07K 2319/33* (2013.01); *C12N 2310/20* (2017.05); *C12N 2510/00* (2013.01); *C12N 2750/14143* (2013.01); *C12N 2800/80* (2013.01)

(58) Field of Classification Search
CPC ....... A61P 35/02; A61P 35/17; C07K 14/7051
See application file for complete search history.

(56) References Cited

FOREIGN PATENT DOCUMENTS

WO 2017/053729 A1 3/2017

OTHER PUBLICATIONS

Eyquem et al. 2017; Targeting a CAR to the TRAC locus iwht CRISPR/Cas9 enhances tumor rejection. Nature. 543(7643): 113-117 ; Author Manuscript, pp. 1-28.*
Qasim, et al., Molecular Remission of Infant B-ALL After Infusion of Universal TALEN Gene-Edited CAR T Cells, Science Translational Medicine, 9, eaaj2013 (2017), pp. 1-9.
Qasim W., Allogenic CAR T Cell Therapies for Leukemia, American J Hematol, 2019;94:S50-S54, https://doi.org/10.1002/ajh.25399.
Osborn, et al., Evaluation of TCR Gene Editing Achieved by TALENs, CRISPR/Cas9, and megaTAL Nucleases, Molecular Therapy, vol. 24, No. 3, Mar. 2016, pp. 570-581.
MacLeod, et al., Integration of a CD19 CAR into the TCR Alpha Chain Locus Streamlines Production of Allogeneic Gene-Edited CAR T Cells, Molecular Therapy, vol. 25, No. 4, Apr. 2017, pp. 949-961.

* cited by examiner

*Primary Examiner* — Suzanne M Noakes
(74) *Attorney, Agent, or Firm* — Kilpatrick Townsend & Stockton LLP

(57) ABSTRACT

Methods and compositions for modifying allogeneic donor αβ T cells for use in the treatment of high risk leukemias are provided.

19 Claims, 14 Drawing Sheets
Specification includes a Sequence Listing.

| Name | gRNA target sequence (5'-3') | Gene name | Function |
|---|---|---|---|
| On-target | GAGAATCAAAATCGGTGAATAGG | TRAC | exon (exon 2 of 5) |
| OT1 | TAGAGTTGAAAATCGGTGAATAGG | PUDP | intergenic |
| OT2 | ATCAATCAAATTCGGTGAATTGG | LOC105755953 | intergenic |
| OT3 | ACGAATTAAAATTGGTGAATTGG | LINC01898 | intergenic |
| OT4 | GAAAAGCAAAATAGGTGAATGGG | AJAP1 | intergenic |
| OT5 | AAGAAAAAAATAGGTGAATTGG | VPS13A-AS1 | intron (NM_001018037, intron 1 of 70) |
| OT6 | AAAAACAAAATCAGTGAATTGG | PIK3R1 | intergenic |
| OT7 | CAGCTTCAAAATCTGTGAATGGG | LINC01854 | intron (NR_122040, intron 1 of 4) |
| OT8 | GAGAAAAAAATCAGTGAATTGG | CYP1B1-AS1 | intergenic |
| OT9 | GAGAAGAAAATCAGTGAATTGG | NKX2-2 | intergenic |
| OT10 | AAAAATCAATATCTGTGAATGGG | GALC | intergenic |
| OT11 | TAAAATCAAAAGGGGTGAATTGG | SYPL1 | intron (NM_006754, intron 2 of 5) |
| OT12 | GAGTATGAAAATCGCTGAATAGG | NEBL | intron (NM_213569, intron 2 of 6) |
| OT13 | CAGAAGAAAATCGATGAATTGG | AHNAK | intron (NM_024060, intron 5 of 5) |
| OT14 | CAGAATCATAATACGTGAATTGG | LINC02027 | intergenic |
| OT15 | AAGAATAAAAATTGATGAATTGG | FLJ43315 | intergenic |
| OT16 | AAGAATAAAAATTGATGAATTGG | TEXT4P2 | intergenic |
| OT17 | AAGAATAAAAATTGATGAATTGG | LOC442028 | intron (NR_037597, intron 7 of 9) |
| OT18 | AAGAATAAAAATTGATGAATTGG | FRG1BP | intergenic |
| OT19 | TATAATCAAAATTGGAGAATAGG | LRRK2 | intron (NM_198578, intron 21 of 50) |
| OT20 | TAGAATCAGAATAGGAGAATGGG | LINC01361 | promoter-TSS (NR_110633) |
| OT21 | AAGAATCATTATCGGTAAATTGG | GSE1 | intergenic |
| OT22 | AAAACCAAAATCGGTGTATCGG | GATA3 | intron (NM_002051, intron 3 of 5) |
| OT23 | AAGAAACAAAACGGTGAGTTGG | RP1L1 | exon (NM_178857, exon 3 of 4) |
| OT24 | TAGAATCTAAATTGGTGACTCGG | CADPS | intron (NM_183394, intron 3 of 27) |
| OT25 | AAGTATAAAAATCGGTGAAAGGG | LOC100506403 | intergenic |
| OT26 | TAGAATCAGAATTGGTGACTAGG | LOC101929452 | intergenic |
| OT27 | TAGAATCAGAATTGGTGATTTGG | LINC01029 | intergenic |
| OT28 | CAGAATAAAACTCGGTGAACAGG | IMMP2L | intron (NM_032549, intron 5 of 5) |
| OT29 | CTGAATCAAAATCAGTGAAGTGG | ADD2 | intron (NM_017482, intron 1 of 12) |
| OT30 | AATAATCAAAATCCGTGAAAAGG | DIO2-AS1 | intron (NR_038355, intron 8 of 8) |
| OT31 | TAGAATCAGAATCAGTGAAAGGG | MIR1269A | intergenic |
| OT32 | AAGAATCAATATCAGTGAAATGG | EBF2 | intergenic |
| OT33 | AAGAATCAACATCGTTGAAAGGG | ZNF292 | intergenic |
| OT34 | AAGAATCAATATCGTTGAAATGG | SLITRK6 | intergenic |
| OT35 | TAGAATCAAAATAGCTGAACTGG | FAM41AY1 | intergenic |
| OT36 | GAGCATCAAAATCGGTAAAGAGG | GABRA3 | intron (NM_000808, intron 3 of 9) |
| OT37 | AAGAATCAAAATCCTTGAAATGG | PABPC5-AS1 | intergenic |
| OT38 | AGGAATCAAAATGGGTGAATGAG | DNAH14 | intron (NM_001373, intron 62 of 83) |
| OT39 | AAGAATGAAAATTGGTGAATTAG | LEXR1 | intron (NM_001004316, intron 5 of 12) |
| OT40 | CAGAATGAAAATCAGTGAATGAG | TMEM388 | intergenic |

FIG. 5A

SEQUENCE LISTING

<160> NUMBER OF SEQ ID NOS: 51

<210> SEQ ID NO 1
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1
gagaaucaaa aucggugaauu guuuuagagc uagaaauagc aaguuaaaau aaggcuaguc        60
cguuaucaac uugaaaaagu ggcaccgagu cggugcuuuu                              100

<210> SEQ ID NO 2
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aaucaaaauc ggugaauguu uuagagcuag aaauagcaag uuaaaauaag gcuaguccgu        60
uaucaacuug aaaagugc accgagucgg ugc                                       93

<210> SEQ ID NO 3
<211> LENGTH: 23
<212> TYPE: DNA
<213> ORGANISM: Homo sapiens

<400> SEQUENCE: 3
gagaatcaaa atcggtgaat agg                                                23

<210> SEQ ID NO 4
<211> LENGTH: 23
<212> TYPE: DNA
<213> ORGANISM: Homo sapiens

<400> SEQUENCE: 4
tagagttgaa atcggtgaat agg                                                23

<210> SEQ ID NO 5
<211> LENGTH: 23
<212> TYPE: DNA
<213> ORGANISM: Homo sapiens

<400> SEQUENCE: 5
atcaatcaaa ttcggtgaat tgg                                                23

<210> SEQ ID NO 6
<211> LENGTH: 23
<212> TYPE: DNA
<213> ORGANISM: Homo sapiens

<400> SEQUENCE: 6
acgaattaaa attggtgaat tgg                                                23

<210> SEQ ID NO 7
<211> LENGTH: 23
<212> TYPE: DNA
<213> ORGANISM: Homo sapiens

<400> SEQUENCE: 7

-continued gaaaagcaaa ataggtgaat ggg                                        23

<210> SEQ ID NO 8
<211> LENGTH: 23
<212> TYPE: DNA
<213> ORGANISM: Homo sapiens

<400> SEQUENCE: 8
aagaaaaaaa ataggtgaat tgg                                        23

<210> SEQ ID NO 9
<211> LENGTH: 23
<212> TYPE: DNA
<213> ORGANISM: Homo sapiens

<400> SEQUENCE: 9
aaaaaacaaa atcagtgaat tgg                                        23

<210> SEQ ID NO 10
<211> LENGTH: 23
<212> TYPE: DNA
<213> ORGANISM: Homo sapiens

<400> SEQUENCE: 10
cagcttcaaa atctgtgaat ggg                                        23

<210> SEQ ID NO 11
<211> LENGTH: 23
<212> TYPE: DNA
<213> ORGANISM: Homo sapiens

<400> SEQUENCE: 11
gagaaaaaaa atcagtgaat tgg                                        23

<210> SEQ ID NO 12
<211> LENGTH: 23
<212> TYPE: DNA
<213> ORGANISM: Homo sapiens

<400> SEQUENCE: 12
gagaagaaaa atcagtgaat tgg                                        23

<210> SEQ ID NO 13
<211> LENGTH: 23
<212> TYPE: DNA
<213> ORGANISM: Homo sapiens

<400> SEQUENCE: 13
aaaaatcaat atctgtgaat ggg                                        23

<210> SEQ ID NO 14
<211> LENGTH: 23
<212> TYPE: DNA
<213> ORGANISM: Homo sapiens

<400> SEQUENCE: 14
taaaatcaaa aggggtgaat tgg                                        23

<210> SEQ ID NO 15
<211> LENGTH: 23
<212> TYPE: DNA
<213> ORGANISM: Homo sapiens

```
<400> SEQUENCE: 15
gagtatgaaa atcgctgaat agg                                              23

<210> SEQ ID NO 16
<211> LENGTH: 23
<212> TYPE: DNA
<213> ORGANISM: Homo sapiens

<400> SEQUENCE: 16
cagaagaaaa atcgatgaat tgg                                              23

<210> SEQ ID NO 17
<211> LENGTH: 23
<212> TYPE: DNA
<213> ORGANISM: Homo sapiens

<400> SEQUENCE: 17
cagaatcata atacgtgaat tgg                                              23

<210> SEQ ID NO 18
<211> LENGTH: 23
<212> TYPE: DNA
<213> ORGANISM: Homo sapiens

<400> SEQUENCE: 18
aagaataaaa attgatgaat tgg                                              23

<210> SEQ ID NO 19
<211> LENGTH: 23
<212> TYPE: DNA
<213> ORGANISM: Homo sapiens

<400> SEQUENCE: 19
tataatcaaa attggagaat agg                                              23

<210> SEQ ID NO 20
<211> LENGTH: 23
<212> TYPE: DNA
<213> ORGANISM: Homo sapiens

<400> SEQUENCE: 20
tagaatcaga ataggagaat ggg                                              23

<210> SEQ ID NO 21
<211> LENGTH: 23
<212> TYPE: DNA
<213> ORGANISM: Homo sapiens

<400> SEQUENCE: 21
aagaatcatt atcggtaaat tgg                                              23

<210> SEQ ID NO 22
<211> LENGTH: 23
<212> TYPE: DNA
<213> ORGANISM: Homo sapiens

<400> SEQUENCE: 22
aaaaaccaaa atcggtgtat cgg                                              23

<210> SEQ ID NO 23
<211> LENGTH: 23
<212> TYPE: DNA
<213> ORGANISM: Homo sapiens
```

```
<400> SEQUENCE: 23
aagaaacaaa aacggtgagt tgg                                              23

<210> SEQ ID NO 24
<211> LENGTH: 23
<212> TYPE: DNA
<213> ORGANISM: Homo sapiens

<400> SEQUENCE: 24
tagaatctaa attggtgact cgg                                              23

<210> SEQ ID NO 25
<211> LENGTH: 23
<212> TYPE: DNA
<213> ORGANISM: Homo sapiens

<400> SEQUENCE: 25
aagtataaaa atcggtgaaa ggg                                              23

<210> SEQ ID NO 26
<211> LENGTH: 23
<212> TYPE: DNA
<213> ORGANISM: Homo sapiens

<400> SEQUENCE: 26
tagaatcaga attggtgact agg                                              23

<210> SEQ ID NO 27
<211> LENGTH: 23
<212> TYPE: DNA
<213> ORGANISM: Homo sapiens

<400> SEQUENCE: 27
tagaatcaga attggtgatt tgg                                              23

<210> SEQ ID NO 28
<211> LENGTH: 23
<212> TYPE: DNA
<213> ORGANISM: Homo sapiens

<400> SEQUENCE: 28
cagaataaaa ctcggtgaac agg                                              23

<210> SEQ ID NO 29
<211> LENGTH: 23
<212> TYPE: DNA
<213> ORGANISM: Homo sapiens

<400> SEQUENCE: 29
ctgaatcaaa atcagtgaag tgg                                              23

<210> SEQ ID NO 30
<211> LENGTH: 23
<212> TYPE: DNA
<213> ORGANISM: Homo sapiens

<400> SEQUENCE: 30
aataatcaaa atccgtgaaa agg                                              23

<210> SEQ ID NO 31
<211> LENGTH: 23
<212> TYPE: DNA
```

<213> ORGANISM: Homo sapiens

<400> SEQUENCE: 31
tagaatcaga atcagtgaaa ggg    23

<210> SEQ ID NO 32
<211> LENGTH: 23
<212> TYPE: DNA
<213> ORGANISM: Homo sapiens

<400> SEQUENCE: 32
aagaatcaat atcagtgaaa tgg    23

<210> SEQ ID NO 33
<211> LENGTH: 23
<212> TYPE: DNA
<213> ORGANISM: Homo sapiens

<400> SEQUENCE: 33
aagaatcaac atcgttgaaa ggg    23

<210> SEQ ID NO 34
<211> LENGTH: 23
<212> TYPE: DNA
<213> ORGANISM: Homo sapiens

<400> SEQUENCE: 34
aagaatcaat atcgttgaaa tgg    23

<210> SEQ ID NO 35
<211> LENGTH: 23
<212> TYPE: DNA
<213> ORGANISM: Homo sapiens

<400> SEQUENCE: 35
tagaatcaaa atagctgaac tgg    23

<210> SEQ ID NO 36
<211> LENGTH: 23
<212> TYPE: DNA
<213> ORGANISM: Homo sapiens

<400> SEQUENCE: 36
gagcatcaaa atcggtaaag agg    23

<210> SEQ ID NO 37
<211> LENGTH: 23
<212> TYPE: DNA
<213> ORGANISM: Homo sapiens

<400> SEQUENCE: 37
aagaatcaaa atcgttgaaa tgg    23

<210> SEQ ID NO 38
<211> LENGTH: 23
<212> TYPE: DNA
<213> ORGANISM: Homo sapiens

<400> SEQUENCE: 38
aggaatcaaa atgggtgaat gag    23

<210> SEQ ID NO 39
<211> LENGTH: 23

```
<212> TYPE: DNA
<213> ORGANISM: Homo sapiens

<400> SEQUENCE: 39
aagaatgaaa attggtgaat tag                                          23

<210> SEQ ID NO 40
<211> LENGTH: 23
<212> TYPE: DNA
<213> ORGANISM: Homo sapiens

<400> SEQUENCE: 40
cagaatgaaa atcagtgaat gag                                          23

<210> SEQ ID NO 41
<211> LENGTH: 23
<212> TYPE: DNA
<213> ORGANISM: Homo sapiens

<400> SEQUENCE: 41
tctctcagct ggtacacggc agg                                          23

<210> SEQ ID NO 42
<211> LENGTH: 23
<212> TYPE: DNA
<213> ORGANISM: Homo sapiens

<400> SEQUENCE: 42
ctctcagctg gtacacggca ggg                                          23

<210> SEQ ID NO 43
<211> LENGTH: 23
<212> TYPE: DNA
<213> ORGANISM: Homo sapiens

<400> SEQUENCE: 43
tggatttaga gtctctcagc tgg                                          23

<210> SEQ ID NO 44
<211> LENGTH: 23
<212> TYPE: DNA
<213> ORGANISM: Homo sapiens

<400> SEQUENCE: 44
tcagggttct ggatatctgt ggg                                          23

<210> SEQ ID NO 45
<211> LENGTH: 23
<212> TYPE: DNA
<213> ORGANISM: Homo sapiens

<400> SEQUENCE: 45
taggcagaca gacttgtcac tgg                                          23

<210> SEQ ID NO 46
<211> LENGTH: 23
<212> TYPE: DNA
<213> ORGANISM: Homo sapiens

<400> SEQUENCE: 46
acacggcagg gtcagggttc tgg                                          23

<210> SEQ ID NO 47
```

```
<211> LENGTH: 23
<212> TYPE: DNA
<213> ORGANISM: Homo sapiens

<400> SEQUENCE: 47
gctggtacac ggcagggtca ggg                                          23

<210> SEQ ID NO 48
<211> LENGTH: 23
<212> TYPE: DNA
<213> ORGANISM: Homo sapiens

<400> SEQUENCE: 48
gtcagggttc tggatatctg tgg                                          23

<210> SEQ ID NO 49
<211> LENGTH: 23
<212> TYPE: DNA
<213> ORGANISM: Homo sapiens

<400> SEQUENCE: 49
agctggtaca cggcagggtc agg                                          23

<210> SEQ ID NO 50
<211> LENGTH: 23
<212> TYPE: DNA
<213> ORGANISM: Homo sapiens

<400> SEQUENCE: 50
agagtctctc agctggtaca cgg                                          23

<210> SEQ ID NO 51
<211> LENGTH: 23
<212> TYPE: DNA
<213> ORGANISM: Homo sapiens

<400> SEQUENCE: 51
atttgtttga gaatcaaaat cgg                                          23
```

GENOME EDITING OF GRAFT-DERIVED T-CELLS FOR POST-TRANSPLANT IMMUNOTHERAPY

CROSS-REFERENCE TO RELATED APPLICATION

This application claims the benefit of U.S. Provisional Patent Application No. 62/934,994, filed Nov. 13, 2019, which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Feb. 16, 2021, is named 2021-03-04_SEQ-LIST-079445-1211559-3210US_SL.txt and is 7,993 bytes in size.

BACKGROUND

Despite improvements over the last decades, treatment outcomes remain unfavorable in pediatric patients with relapsed or refractory B cell precursor acute lymphoblastic leukemia (r/r BCP-ALL) (1, 2). Allogeneic HSCT has been successfully employed to treat high-risk leukemias (3), which provides a graft-versus-leukemia ("GvL") (4) effect but simultaneously increases the risk for graft-versus-host disease GvHD (5). In order to overcome the challenge of limited donor availability (6), innovative protocols have been developed that allow the use of grafts from haploidentical donors. A successful strategy for haploidentical transplantation is based on the selective elimination of αβ T-cells and CD19$^+$ B-cells (αβ haplo-HSCT) (7), which is associated with a very low incidence of transplantation-related mortality (TRM) and GvHD (FIG. 1A) (8-10). In contrast to CD34$^+$ selection, this manipulation method allows the transfer not only of donor HSCs to the recipient, but also committed hematopoietic progenitors as well as mature natural killer (NK) and γδ T-cells (11, 12), which may provide a protective effect against leukemia relapse and reduce the risk of infectious complications (13). With significant improvement in non-relapse mortality (NRM), disease relapse has become the most important cause of treatment failure in patients with malignancies undergoing αβ haplo-HSCT (8). In particular, the outcome of αβ haplo-HSCT in children with leukemia not in complete remission (CR) or beyond second CR has been poor (9, 14). For this reason, it is necessary to develop novel strategies to reduce leukemic relapse after haplo-HSCT, without increasing the incidence of GvHD or TRM.

An intriguing approach to reducing leukemic relapse is to follow haplo-HSCT with subsequent anti-leukemic cell therapy (15) derived from the stem cell donor (FIGS. 1A-1D), since these cells are from healthy immune systems and are also syngeneic (functionally autologous) to the donor graft, rendering them resistant to immune rejection after transplantation. While the infusion of donor-derived T cells (donor leukocyte infusion, DLI) has been used in various contexts to enhance antileukemic efficacy (FIG. 1B), it is accompanied by a high risk of severe GvHD (16-22). An improvement over DLI is to genetically engineer the donor T-cells with a safety switch (suicide gene) such that the cells can be quickly eliminated if severe GvHD occurs (FIG. 1C).

Early trials have suggested that this strategy does help prevent relapse and if GvHD occurs, the suicide switch (inducible caspase 9 (iC9-T cells)) is effective at eliminating alloreactive cells (23-25). Although this strategy allows the control of GvHD after it occurs, the beneficial effect of GvL and the risk of GvHD are still linked to each other. It would be an improvement, therefore, to establish an approach that provides antileukemic activity without GvHD.

Chimeric antigen receptors (CAR) can redirect T cell cytotoxicity towards cancer-related antigens and achieve remissions in otherwise refractory hematological malignancies expressing these targets (26, 27). Currently, the most commonly used CAR T cell products are manufactured from patient-derived autologous T cells that are harvested and transduced with a semi-randomly integrating viral vector for delivery and expression of the CAR gene, and then infused back into the patient after lymphodepleting therapy (28). This is associated with high variability in the CAR T cell product and manufacturing failures. Furthermore, contaminations of the autologous cells with leukemic cells (29) and the risk of insertional mutagenesis associated with randomly integrating viral vectors (30) are challenges associated with the established approach.

There is therefore a need for new approaches to treating leukemias such as relapsed or refractory B cell precursor acute lymphoblastic leukemia that provide effective antileukemic activity in patients, but without the risk of GvHD. The present disclosure satisfies this need and provides other advantages as well.

BRIEF SUMMARY

In one aspect, the present disclosure provides a method of treating leukemia in a subject that has previously received a hematopoietic stem cell transplant from an HLA-matched donor, the method comprising: i) introducing into a plurality of αβ T cells from the donor a guide RNA targeting the TRAC locus, an RNA-guided nuclease, and a homologous donor template encoding a CD19-specific chimeric antigen receptor (CAR), wherein the RNA-guided nuclease cleaves the endogenous T cell receptor antigen constant (TRAC) locus in the plurality of cells and the polynucleotide is integrated in-frame into the cleaved TRAC locus; ii) expanding the modified T cells in culture to generate a population of modified CAR T cells; and iii) administering the modified CAR T cells to the subject.

In some embodiments, the method further comprises a step in which the plurality of αβ T cells is isolated from the donor prior to the introducing. In some embodiments of the method, the hematopoietic stem cell transplant comprised hematopoietic stem and progenitor cells (HSPCs), NK cells, and γδ T cells, and wherein αβ T cells and B cells, e.g., CD19$^+$ B cells, had been removed from the graft prior to transplantation. In some embodiments, the isolated αβ T cells used in the method correspond to αβ T cells that had been previously removed from the graft prior to the original transplantation. In some embodiments, the guide RNA and the RNA-guided nuclease are introduced into the cells as a ribonucleoprotein (RNP), e.g., by electroporation. In some embodiments, the polynucleotide is introduced into the cells using a recombinant adeno-associated virus (rAAV), e.g., an rAAV serotype 6 vector. In some embodiments, the cells are present at a concentration of at least about 5×10$^6$ cells/ml during the transduction of the rAAV (e.g., rAAV serotype 6) vector. In some embodiments, the cells are maintained for at least about 12 hours at the concentration of at least about 5×10$^6$ cells/ml during the transduction of the rAAV (e.g., rAAV serotype 6) vector. In some embodiments, the multiplicity of infection (MOI) of the rAAV vector is at least about 2500 vg/cell. In some embodiments, the MOI is about 5000 vg/cell.

In some embodiments, the RNA-guided nuclease is Cas9. In some embodiments, the guide RNA targets exon 1 of the TRAC locus. In some embodiments, the guide RNA targets the TRAC-1 sequence. In some embodiments, the CAR comprises a costimulatory domain. In some embodiments, the costimulatory domain comprises CD28. In some embodiments, the introduction of the guide RNA targeting the TRAC locus, the RNA-guided nuclease, and the homologous donor template comprising a polynucleotide encoding a CD19-specific chimeric antigen receptor (CAR) into the plurality of αβ T cells results in a loss of TCR expression in and/or the presence of the CAR on the surface of at least about 70%, 80%, 90%, 95%, or more of the cells.

In some embodiments, the method further comprises a purification step wherein TCR+ cells are selectively eliminated from the population of modified CAR T cells prior to administration to the subject. In some embodiments, the TCR+ cells are selectively eliminated from the population using magnetic bead activated cell sorting (MACS). In some embodiments, the purification step results in a maximum of 0.05% TCR+αβ+ cells in the population prior to administration to the subject. In some embodiments, the method causes a reduction in the leukemia burden in the subject. In some embodiments, the method does not cause substantial graft versus host disease (GvHD) in the subject. In some embodiments, the cells are administered to the subject intravenously. In some embodiments, the subject is a human. In some embodiments the subject is a pediatric patient. In some embodiments, the subject has relapsed or refractory B cell precursor acute lymphoblastic leukemia (r/r BCP-ALL).

In another aspect, the present disclosure provides a modified αβ T cell produced using any of the herein-described methods.

BRIEF DESCRIPTION OF THE DRAWINGS

FIG. 1A: The protocol for haploidentical HSCT with TCR αβ+/CD19+-depletion, which establishes a backbone for additional cellular immunotherapies. FIG. 1B: In order to improve immune reconstitution and enhance anti-leukemic activity, a specified number of T cells is transfused to the patient separate from the graft. FIG. 1C: In order to retain control of the T cells and be able to intervene in the case of severe GvHD, the T cells can be transduced with an inducible suicide system like the herpes simplex virus-derived thymidine kinase (HSV-TK) or the inducible Caspase 9 (iCasp9). FIG. 1D: The αβ T cells are removed from the graft before transplantation and can be used as starting material to create genome edited CAR T cells by targeted integration of a CD19-CAR into the TRAC locus, in order to target residual leukemia after HSCT without causing GvHD. CAR=chimeric antigen receptor, GvHD, =graft-versus-host disease, HSPCs=hematopoietic stem and progenitor cells, TCR=T cell, receptor, NK cells=natural killer cells.

FIG. 2A: Targeting strategy using Cas9 RNP and rAAV6. The sgRNA targets the coding region of the TRAC locus. The donor template carrying homology arms and the transgene is provided by rAAV6. FIG. 2B: Representative plots of FACS phenotyping for cells treated as indicated 4 days after targeting to evaluate efficiency of TCRαβ knockout and NGFR expression. FIG. 2C: Quantification of the populations after targeting of T cells from 11 different donors. FIG. 2D: Representative FACS plot of the cells stained for NGFR and a CD19-CAR idiotype-specific antibody. FIG. 2E: FACS plot showing NGFR and TCRαβ expression after depletion of cells expressing the αβ T cell receptor. FIG. 2F: Quantification of αβ TCR depletion efficiency for 4 different replicates, plotted as mean+/−SD. FIG. 2G: Expansion of T cells during 7 days after gene editing compared to numbers before electroporation using optimized density and MOI for AAV transduction. FIG. 2H: Expansion of T cells (compared to numbers before gene editing) cultured at different densities after electroporation. RNP=ribonucleoprotein, rAAV6=recombinant adeno-associated virus serotype 6, NGFR=nerve growth factor receptor, pA=poly-adenylation signal, 2A=2A peptide.

FIG. 3A: IL-2 and IFNγ concentrations in cell culture supernatant after co-culture of CAR T cells or control cells with CD19+ Nalm6 or Raji cells. Control cells were treated with RNP only (TRAC knockout without CAR expression). Bars and error bars represent mean+/−SD from 3 biological replicates. Asterisks depict levels of significance compared to control cells as analyzed by t tests. FIG. 3B: In vitro cytotoxicity assay of CAR T cells co-cultured for 20 h with Nalm6 or Raji cells (both CD19+ and GFP+) at different effector-to-target (E:T) ratios. Counts of viable cells were assessed for target cells co-cultured with control cells or CAR T cells and the fraction of target cells killed was calculated using samples without effector cells as reference. Bars and error bars represent means+/−SD from 3 biological replicates and asterisks depict levels of significance (t tests). FIG. 3C: Quantification of B cells for differentially treated cell populations on day 1 and day 4 after gene editing, for cell populations that have undergone gene targeting (RNP+ AAV) or control treatments. Groups were compared by t tests and levels of significance indicated by asterisks. FIGS. 3D-3G: Phenotyping of the CAR T cell product, gated on NGFR+ cells. FIG. 3D: Distribution of CD4+ and CD8+ cells. FIG. 3E: Expression of memory and effector T cell markers among CD4+ and CD8+ cells. FIG. 3F: Quantification of CD4/CD8 distribution from 4 biological replicates. Bars and error bars represent mean+/−SD. FIG. 3G: Quantification of the memory/effector populations on cells from 4 different donors. Bars represent mean+/−SD. CAR=chimeric antigen receptor, IFN=interferon, IL=interleukin, RNP=ribonucleoprotein, AAV=adeno-associated virus, NGFR=nerve-growth-factor receptor.

FIG. 4A: Bioluminescence imaging of Nalm6 xenografts in NSG mice treated with genome edited CD19-specific CAR T cells that were manufactured from αβ-TCR+ T cells. The experiment was repeated at the dose level of 5E6 cells per mouse with comparable outcome. FIG. 4B: Kaplan-Meier survival plot of mice treated with control T cells or CAR T cells. Asterisks indicate levels of significance of the CAR T cell group compared to the respective control group (mock) of the same cell dose using logrank tests. CAR=chimeric antigen receptor.

FIGS. 5A-5B. Evaluation of endonuclease specificity. FIG. 5A: Putative off-target sites in the human genome (hg38) determined by COSMID and sorted by predicted relevance in descending order. Mismatches to the target site are marked red. OT 1-37 have 3 relevant mismatches in the protospacer region without InDels and OT sites 38-40 have 2 relevant mismatches and a PAM mismatch. The nucleotide furthest from the PAM was ignored for sorting because of mismatch tolerance at this location by Cas9. FIG. 5A discloses SEQ ID NOS: 3-18, 18, 18 and 18-40, respectively, in order of appearance. FIG. 5B: Human T cells from 6 different donors were electroporated with the high-fidelity Cas9 protein complexed with the sgRNA targeting the TRAC locus (or mock electroporated to determine background). NGS was performed on all predicted OT sites. The dotted line depicts the sensitivity limit attributed to this method of 0.1%. sgRNA=single guide RNA, PAM=protospacer-adjacent motif, OT=off-target, InDel=insertion or deletion.

FIG. 6A: Counts of COSMID predicted off-target sites for sgRNAs in exon 1 of the TRAC locus, ranked from left to right by increasing counts of predicted sites, prioritizing sgRNAs with low numbers of highly-similar off-target sites (low COSMID scores). FIG. 6B: Overview over sgRNAs in exon 1 of TRAC with specificity scores calculated by CRISPOR (MIT algorithm) and COSMID. sgRNA=single guide RNA, PAM=protospacer-adjacent motif. FIG. 6B discloses SEQ ID NOS: 3 and 41-51, respectively, in order of appearance.

FIG. 7A: Expansion after electroporation of CAR T cells or control cells treated with the indicated conditions, relative to their count before electroporation. Cells originated from 2 different donors. FIG. 7B: Titration of different rAAV6 MOIs shows a slight increase in the frequency of targeted cells between 2500 and 5000 vg/cell but no further increase beyond that. FIG. 7C: A strong determinant of targeting frequencies is the duration of transduction at high density (>5×10$^6$ cells per ml) before dilution with medium to the target density for expansion (5×10$^5$ cells per ml). Transduction was performed at the MOI of 5000 vg/cell. FIG. 7D: Detection of B cells 24 h after gene targeting shows early disappearance of CD19$^+$ cells for the condition that leads to CAR expression but not in the control conditions (mock electroporation, RNP electroporation only, AAV transduction only). AAV=adeno-associated virus, RNP=ribonucleoprotein, MOI=multiplicity of infection, NGFR=nerve-growth-factor receptor.

FIG. 8A: Survival graph for Nalm6 xenografts in NSG mice after transplantation of mock treated T cells (Mock), TRAC RNP treated T cells (RNP) or RNP+AAV treated T cells (CAR T) at 5 million cells per mouse. Groups were compared by log-rank test and statistical significance indicated in the graph. FIG. 8B: BLI imaging result on day 15 after injection comparing the 3 groups.

DETAILED DESCRIPTION

1. Introduction

Figures 1A, 1B, 1C, 1D:
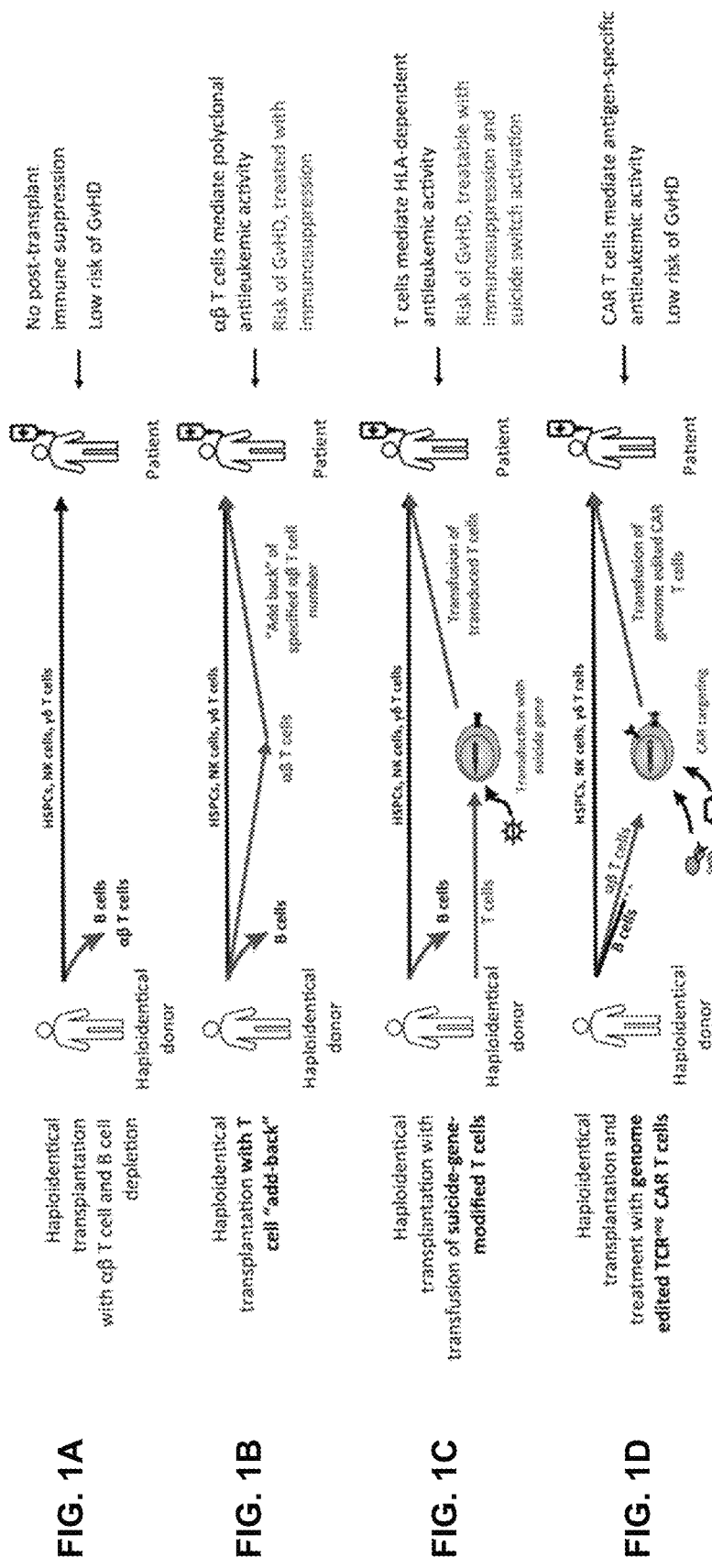
FIGS. 1A-1D. T-cell therapy approaches in combination with TCRαβ+/CD19+-depleted haploidentical stem cell transplantation aiming to decrease relapse rates.

The present disclosure provides methods and compositions for treating leukemias such as relapsed or refractory B cell precursor acute lymphoblastic leukemia in patients, e.g., pediatric patients. The present methods involve the CRISPR-Cas-mediated integration of a CAR, e.g., CD19-specific CAR, at the TRAC locus of αβ T cells from an allogeneic donor, and reintroducing the modified CAR T cells into the patient.

The fact that the CAR T cells are produced from cells originating from the same donor that is used for allogeneic HSCT makes the CAR T cells fully immune-compatible with the immune system that will be established in the patient after engraftment and immune reconstitution. This enables full bidirectional immune tolerance and immune surveillance of the transplanted CAR T cells.

The present methods will make it possible to create CAR T cells and perform quality control on the whole batch, followed by cryopreservation in several fractions that can be thawed and also be used at later time points for multiple doses in the same patient, which allows for response-guided treatment.

2. General

Practicing the disclosed methods utilizes routine techniques in the field of molecular biology. Basic texts disclosing the general methods of use in this disclosure include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb), base pairs (bp), or nucleotides (nt). Sizes of single-stranded DNA and/or RNA can be given in nucleotides. These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

3. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells, and so forth.

The terms "about" and "approximately" as used herein shall generally mean an acceptable degree of error for the quantity measured given the nature or precision of the measurements. Typically, exemplary degrees of error are within 20 percent (%), preferably within 10%, and more preferably within 5% of a given value or range of values. Any reference to "about X" specifically indicates at least the values X, 0.8X, 0.81X, 0.82X, 0.83X, 0.84X, 0.85X, 0.86X, 0.87X, 0.88X, 0.89X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, 1.1X, 1.11X, 1.12X, 1.13X, 1.14X, 1.15X, 1.16X, 1.17X, 1.18X, 1.19X, and 1.2X. Thus, "about X" is intended to teach and provide written description support for a claim limitation of, e.g., "0.98X."

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. The promoter can be a heterologous promoter.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. The promoter can be a heterologous promoter. In the context of promoters operably linked to a polynucleotide, a "heterologous promoter" refers to a promoter that would not be so operably linked to the same polynucleotide as found in a product of nature (e.g., in a wild-type organism).

As used herein, a first polynucleotide or polypeptide is "heterologous" to an organism or a second polynucleotide or polypeptide sequence if the first polynucleotide or polypeptide originates from a foreign species compared to the organism or second polynucleotide or polypeptide, or, if from the same species, is modified from its original form. For example, when a promoter is said to be operably linked to a heterologous coding sequence, it means that the coding sequence is derived from one species whereas the promoter sequence is derived from another, different species; or, if both are derived from the same species, the coding sequence is not naturally associated with the promoter (e.g., is a genetically engineered coding sequence).

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The terms "expression" and "expressed" refer to the production of a transcriptional and/or translational product, e.g., of an encoded CAR. In some embodiments, the term refers to the production of a transcriptional and/or translational product encoded by a gene or a portion thereof. The level of expression of a DNA molecule in a cell may be assessed on the basis of either the amount of corresponding mRNA that is present within the cell or the amount of protein encoded by that DNA produced by the cell.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. In some cases, conservatively modified variants of a protein can have an increased stability, assembly, or activity as described herein.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or specified subsequences that are the same. Two sequences that are "substantially identical" have at least 60% identity, preferably 65%, 70%, 75%, 80%, 85%, 90%, 91%, 92%, 93, 94%, 95%, 96%, 97%, 98%, 99%, or 100% identity, when compared and aligned for maximum correspondence over a comparison window, or designated region as measured using a sequence comparison algorithm or by manual alignment and visual inspection where a specific region is not designated. With regard to polynucleotide sequences, this definition also refers to the complement of a test sequence. With regard to amino acid sequences, in some cases, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST 2.0 algorithm and the default parameters discussed below are used.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

An algorithm for determining percent sequence identity and sequence similarity is the BLAST 2.0 algorithm, which is described in Altschul et al., (1990) *J. Mol. Biol.* 215: 403-410. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The "CRISPR-Cas" system refers to a class of bacterial systems for defense against foreign nucleic acids. CRISPR-Cas systems are found in a wide range of bacterial and archaeal organisms. CRISPR-Cas systems fall into two classes with six types, I, II, III, IV, V, and VI as well as many sub-types, with Class 1 including types I and III CRISPR systems, and Class 2 including types II, IV, V and VI; Class 1 subtypes include subtypes I-A to I-F, for example. See, e.g., Fonfara et al., *Nature* 532, 7600 (2016); Zetsche et al., *Cell* 163, 759-771 (2015); Adli et al. (2018). Endogenous CRISPR-Cas systems include a CRISPR locus containing repeat clusters separated by non-repeating spacer sequences that correspond to sequences from viruses and other mobile genetic elements, and Cas proteins that carry out multiple functions including spacer acquisition, RNA processing from the CRISPR locus, target identification, and cleavage. In class 1 systems these activities are effected by multiple Cas proteins, with Cas3 providing the endonuclease activity, whereas in class 2 systems they are all carried out by a single Cas, Cas9.

A "homologous repair template" refers to a polynucleotide sequence that can be used to repair a double stranded break (DSB) in the DNA, e.g., a CRISPR/Cas9-mediated break at the TRAC locus as induced using the herein-described methods and compositions. The homologous repair template comprises homology to the genomic sequence surrounding the DSB, i.e., comprising TRAC homology arms as described herein. In some embodiments, two distinct homologous regions are present on the template, with each region comprising at least 50, 100, 200, 300, 400, 500, 600, 700, 800, 900 or more nucleotides or more of homology with the corresponding genomic sequence. In particular embodiments, the templates comprise two homology arms comprising about 500 nucleotides of homology extending from either site of the sgRNA target site. The repair template can be present in any form, e.g., on a plasmid that is introduced into the cell, as a free floating doubled stranded DNA template (e.g., a template that is liberated from a plasmid in the cell), or as single stranded DNA. In particular embodiments, the template is present within a viral vector, e.g., an adeno-associated viral vector such as AAV6. The templates described herein also comprise a coding sequence encoding a CD19-specific CAR.

As used herein, "homologous recombination" or "HR" refers to insertion of a nucleotide sequence during repair of double-strand breaks in DNA via homology-directed repair mechanisms. This process uses a "donor template" or "homologous repair template" with homology to nucleotide sequence in the region of the break as a template for repairing a double-strand break. The presence of a double-stranded break facilitates integration of the donor sequence. The donor sequence may be physically integrated or used as a template for repair of the break via homologous recombination, resulting in the introduction of all or part of the nucleotide sequence. This process is used by a number of different gene editing platforms that create the double-strand break, such as meganucleases, such as zinc finger nucleases (ZFNs), transcription activator-like effector nucleases (TALENs), and the CRISPR-Cas9 gene editing systems. In particular embodiments, HR involves double-stranded breaks induced by CRISPR-Cas9.

The TRAC locus or gene, or T Cell Receptor Alpha Constant locus or gene (NCBI Gene ID 28755 and UniProt P01848, the entire disclosures of which are herein incorporated by reference), encodes the constant region of the T Cell Receptor Alpha chain, which forms part of $\alpha\beta$ T cell receptors. Disruption of the TRAC locus using the present methods results, e.g., in a loss of expression of the TCR alpha chain, and consequently an absence of TCR receptors on the surface of the cells.

CD19 refers to a gene encoding a surface protein on B cell lymphocytes. The encoded protein has two N-terminal extracellular Ig-like domains, separated by a non-Ig-like domain, as well as a hydrophobic transmembrane domain and a large C-terminal cytoplasmic domain. The protein forms a complex with several membrane proteins including complement receptor type 2 (CD21) and tetraspanin (CD81). The CD19-specific CAR receptors described herein can specifically bind to any one or more parts of the protein, e.g., to antigens present on the B cell surface. The NCBI Gene ID number for CD19 is 930, the entire disclosure of which is herein incorporated by reference.

CD28 (NCBI Gene ID No. 940, the entire disclosure of which is herein incorporated by reference) is a gene encoding a protein that is essential for T-cell proliferation and survival, cytokine production, and T-helper type 2 development. The CD28 polypeptides as used herein, e.g., as a costimulatory domain within the CAR, contribute to the activation and proliferation of the herein-described CAR T cells.

A CAR, or Chimeric Antigen Receptor, is a receptor protein that has been engineered to give T cells the ability to specifically recognize a particular antigen. CARs comprise both antigen-binding and T-cell activating functions (see, e.g., Feins et al. (2019) Am. J. Hematol. 94(S1):S3-S9; Guedan et al., (2018) Meth. & Clin. Dev. 12: 145-156; Sadelain (2017) Ann. Rev. Cancer Biol. 1:447-466; Daga & Davila (2016) Mol. Ther. Oncol. 3:16014; the entire disclosures of which are herein incorporated by reference). CARs comprise an extracellular ligand-binding domain, e.g., an scFv, a spacer domain, a transmembrane domain, and one or more cytoplasmic domains. CARs as used herein can refer to any type or variant of CAR, including first generation CARs (e.g., comprising a single activatory domain, such as a CD3$\zeta$ cytoplasmic domain, or $\gamma$ chain of Fc receptor), second generation CARs (e.g., comprising an activatory domain, e.g., CD3$\zeta$ or $\gamma$ chain of an Fc receptor, as well as one or more co-stimulatory domains from, e.g., CD28 or 4-1BB), or third generation CARs. In particular embodiments, the CAR receptor used in the present methods comprises a co-stimulatory domain. In particular such embodiments, the co-stimulatory domain comprises or is derived from CD28. CD19-specific CARs are CARs that can specifically bind to a CD19 protein or fragment thereof. In the present methods, polynucleotides encoding a CAR that can specifically recognize CD19 are introduced into the TRAC locus in $\alpha\beta$ T cells isolated from, e.g., an allogeneic donor, wherein the polynucleotide replaces or disrupts the TRAC locus. As a result, the modified $\alpha\beta$ T cell expressed the CAR but no longer expresses the T cell receptor alpha chain (and the endogenous TCR is therefore no longer present on the cell surface).

4. Isolation and Genetic Modification of $\alpha\beta$ T Cells

Subjects and Cells

The present methods can be used in any patients who have an indication for haploidentical HSCT for the treatment of otherwise refractory or relapsed ALL. In some embodiments of the present disclosure, allogeneic HSCT can also be performed from donors matched only for one HLA haplotype if the donor-derived, potentially alloreactive T cells are depleted. The present methods are based on $\alpha\beta$ haplo-HSCT, in which $\alpha\beta^+$ T cells and CD19$^+$ cells are removed from the graft prior to infusion to the patient. This strategy makes large numbers of potentially alloreactive $\alpha\beta^+$ T cells available, which are otherwise discarded but can be recovered and used to create cell-based immunotherapies.

The subject can be any subject, e.g. a human or other mammal, with an indication for haploidentical HSCT for the treatment of otherwise refractory or relapsed ALL. In some embodiments, the subject is a human. In some embodiments, the subject is an adult. In some embodiments, the subject is a child (e.g., a child with leukemia). In some embodiments, the subject is female (e.g., an adult female). In some embodiments, the subject is male (e.g., an adult male).

In particular embodiments, integration of a CAR through genome editing redirects them to target the CD19 antigen, but the methods can be applied to other cancer-associated antigens as well. Engagement of the antigen leads to activation of the CAR T cell, thereby redirecting cytotoxicity towards the malignant cells. At the same time, the allogeneic CAR T cells are prevented from causing GvHD by disruption of the gene encoding for the T cell receptor alpha chain, which leads to loss of the endogenous T cell receptor from the cell surface.

The combination of donor-derived TCR$^-$ CAR T cells with HSCT allows the use of T cells from allogeneic donors, which avoids the challenges of autologous CAR T cell therapies. In particular, using the present methods, T cells from healthy donors that become available in large numbers during the HSCT procedure can be processed and cell manufacturing, expansion and quality control performed, while the patient is undergoing the haplo-HSCT procedure. Consecutively, the CAR T cells can be infused into the patient before immune recovery is completed, without additional need for lymphodepletion. The possibility to manufacture multiple batches of CAR T cells makes it possible to store additional cell doses for usage whenever indicated.

The present methods involve, e.g., ex-vivo graft manipulation to remove T cells expressing the TCR alpha and beta chains from the other hematopoietic cells. CD19$^+$ cells can also be depleted to prevent post-transplantation lymphoproliferation. When the remaining cells are transfused into the recipient, the cell fraction containing the TCR $\alpha\beta^+$ cells is preserved, expanded in culture, and genome editing is used to integrate a CD19-specific CAR in-frame into the TRAC locus. This leads to disruption of the targeted gene (TRAC), leading to loss of the T cell receptor on the cell surface while allowing expression of the CAR. The integration of the construct into the TRAC locus for CAR T generation provides two major advantages: first, this strategy avoids the variability in CAR expression levels and the potential risk for insertional mutagenesis associated with randomly-integrating viral vectors traditionally used to transduce the CAR construct. In addition, knockout of the TCR creates a CAR T product without alloreactivity with demonstrated antigen-specific activity against leukemic cells.

The resulting CAR T cells (termed "αβ TCR-CD19 CAR-T") can be used, e.g., for patients with malignancies that express the CD19 antigen (e.g., acute lymphoblastic leukemia) and undergo haplo-HSCT.

In some embodiments, αβ haplo-HSCT donors receive, e.g., granulocyte-colony stimulating factor (G-CSF) for 4 days with or without a CXCR4 antagonist (Plerixafor, Mozobil), and apheresis is performed on, e.g., the 5th day. TCR αβ$^+$ and CD19$^+$ cells are then coupled with antibodies and magnetic beads and isolated on a column in a magnetic field. The remaining graft is transplanted to the recipient who has undergone myeloablative conditioning.

Genetic Modification of the Cells

In particular embodiments, the TCR αβ$^+$/CD19$^+$ cell fraction (non-target fraction from the graft manipulation procedure) is cultured and activated with, e.g., anti-CD3/-CD28 magnetic beads and IL-2. Genome editing is performed by creating a targeted DNA double-strand break in the TRAC gene by electroporating, e.g., Cas9 ribonucleoprotein (RNP) in complex with a TRAC-specific sgRNA, and providing a DNA repair donor template by transducing, e.g., a recombinant adeno-associated virus (rAAV) serotype 6. The vector carries homology arms flanking the targeted region and a transgene that integrates a CD19-specific CAR with or without a promotor, with or without a selectable marker, and with or without a suicide gene. The cells are expanded over at least 3 days. At this time point, the majority of the cells have lost expression of the T cell receptor from the cell surface and are expressing the CAR. Before their use in a patient, remaining TCRαβ$^+$ cells are removed by magnetic bead labelling and passing through a column in a magnetic field. Suitable methods for targeting the TRAC locus with a CAR, e.g., a CD19-specific CAR, are described, e.g., in McLeod et al. (2017) Mol. Ther. (25(4): 949-961, and Eyquem et al. (2017) Nature 543(7643):113-117), the entire disclosures of which are herein incorporated by reference.

Guide RNAs

The guide RNAs, e.g., single guide RNAs (sgRNAs), used in the present methods target the TRAC locus. sgRNAs interact with a site-directed nuclease such as Cas9 and specifically bind to or hybridize to a target nucleic acid within the genome of a cell, such that the sgRNA and the site-directed nuclease co-localize to the target nucleic acid in the genome of the cell. The sgRNAs as used herein comprise a targeting sequence comprising homology (or complementarity) to a target DNA sequence at the TRAC locus, and a constant region that mediates binding to Cas9 or another RNA-guided nuclease. The sgRNA can target any sequence within TRAC adjacent to a PAM sequence. Suitable guide RNAs for targeting the TRAC locus with a CAR, e.g., a CD19-specific CAR, are described, e.g., in McLeod et al. (2017) Mol. Ther. (25(4):949-961, and Eyquem et al. (2017) Nature 543(7643):113-117), the entire disclosures of which are herein incorporated by reference. In particular embodiments, the sgRNA targets exon-1 of the TRAC locus. In particular embodiments, the sgRNA comprises or targets the TRAC-1 sequence (see, e.g., Osborn et al. (2016) Mol. Ther. 24(3):570-581, the entire disclosure of which is herein incorporated by reference). In particular embodiments, the sgRNA has few or no detectable off-target sites in the genome. In some embodiments, the guide RNA comprises, or is complementary to, all or a fragment of one of the sequences GAGAAUCAAAAUCGGUGAAUGUUUUAGAGC-UAGAAAUAGCAAGUUAAAAUAAGG CUAGU-CCGUUAUCAACUUGAAAAAGUGGCACCGA-GUCGGUGCUUUU (SEQ ID NO: 1), or AAUCAAAAUCGGUGAAUGUUUUAGAGCUA-GAAAUAGCAAGUUAAAAUAAGGCUA GUCCGUUAUCAAC-UUGAAAAAGUGGCACCGAGUCGGUGC (SEQ ID NO: 2), or to one of the sequences with, e.g., 1, 2, 3 or more nucleotide substitutions.

In some embodiments, the sgRNAs comprise one or more modified nucleotides. For example, the polynucleotide sequences of the sgRNAs may also comprise RNA analogs, derivatives, or combinations thereof. For example, the probes can be modified at the base moiety, at the sugar moiety, or at the phosphate backbone (e.g., phosphorothioates). In some embodiments, the sgRNAs comprise 3' phosphorothiate internucleotide linkages, 2'-O-methyl-3'-phosphoacetate modifications, 2'-fluoro-pyrimidines, S-constrained ethyl sugar modifications, or others, at one or more nucleotides. In particular embodiments, the sgRNAs comprise 2'-O-methyl-3'-phosphorothioate (MS) modifications at one or more nucleotides (see, e.g., Hendel et al. (2015) Nat. Biotech. 33(9):985-989, the entire disclosure of which is herein incorporated by reference). In particular embodiments, the 2'-O-methyl-3'-phosphorothioate (MS) modifications are at the three terminal nucleotides of the 5' and 3' ends of the sgRNA.

The sgRNAs can be obtained in any of a number of ways. For sgRNAs, primers can be synthesized in the laboratory using an oligo synthesizer, e.g., as sold by Applied Biosystems, Biolytic Lab Performance, Sierra Biosystems, or others. Alternatively, primers and probes with any desired sequence and/or modification can be readily ordered from any of a large number of suppliers, e.g., ThermoFisher, Biolytic, IDT, Sigma-Aldrich, GeneScript, etc.

RNA-Guided Nucleases

Any CRISPR-Cas nuclease can be used in the method, i.e., a CRISPR-Cas nuclease capable of interacting with a guide RNA and cleaving the DNA at the target site as defined by the guide RNA. In some embodiments, the nuclease is Cas9 or Cpf1. In particular embodiments, the nuclease is Cas9. The Cas9 or other nuclease used in the present methods can be from any source, so long that it is capable of binding to an sgRNA described herein and being guided to and cleaving the specific TRAC sequence targeted by the targeting sequence of the sgRNA. In particular embodiments, the Cas9 is from *Streptococcus pyogenes*.

Also disclosed herein are CRISPR/Cas or CRISPR/Cpf1 systems that target and cleave DNA at the TRAC locus. An exemplary CRISPR/Cas system comprises (a) a Cas (e.g., Cas9) or Cpf1 polypeptide or a nucleic acid encoding said polypeptide, and (b) an sgRNA that hybridizes specifically to the TRAC locus, or a nucleic acid encoding said guide RNA. In some instances, the nuclease systems described herein, further comprises a donor template as described herein. In particular embodiments, the CRISPR/Cas system comprises an RNP comprising an sgRNA targeting TRAC and a Cas protein such as Cas9. In some embodiments, a high fidelity version of Cas9 is used (see, e.g., Vakulskas et al. (2018) Nat. Med. 24(8):1216-1224, the entire disclosure of which is herein incorporated by reference).

In addition to the CRISPR/Cas9 platform (which is a type II CRISPR/Cas system), alternative systems exist including type I CRISPR/Cas systems, type III CRISPR/Cas systems, and type V CRISPR/Cas systems. Various CRISPR/Cas9 systems have been disclosed, including *Streptococcus pyogenes* Cas9 (SpCas9), *Streptococcus thermophilus* Cas9 (StCas9), *Campylobacter jejuni* Cas9 (CjCas9) and *Neisseria cinerea* Cas9 (NcCas9) to name a few. Alternatives to the Cas system include the *Francisella novicida* Cpf1 (FnCpf1), *Acidaminococcus* sp. Cpf1 (AsCpf1), and Lachnospiraceae bacterium ND2006 Cpf1 (LbCpf1) systems. Any of the above CRISPR systems may be used to induce a single or double stranded break at the TRAC locus to carry out the methods disclosed herein.

Introducing the sgRNA and Cas Protein into Cells

The sgRNA and nuclease can be introduced into a cell using any suitable method, e.g., by introducing one or more polynucleotides encoding the sgRNA and the nuclease into the cell, e.g., using a vector such as a viral vector or delivered as naked DNA or RNA, such that the sgRNA and nuclease are expressed in the cell. In particular embodiments, the sgRNA and nuclease are assembled into ribonucleoproteins (RNPs) prior to delivery to the cells, and the RNPs are introduced into the cell by, e.g., electroporation. In particular embodiments, the cells are cultured and stimulated as described elsewhere herein, and electroporated with the RNPs. In particular embodiments, the electroporation is followed, e.g., immediately followed, by the transduction of a homologous repair template, e.g., as administered using a viral vector, e.g., a non-integrating recombinant adeno-associated virus serotype 6 (AAV6) vector.

In some embodiments, i53 (Canny et al. (2018) *Nat Biotechnol* 36:95) is introduced into the cell in order to promote integration of the donor template by homology directed repair (HDR) versus integration by non-homologous end-joining (NHEJ). For example, an mRNA encoding i53 can be introduced into the cell, e.g., by electroporation at the same time as an sgRNA-Cas9 RNP. The sequence of i53 can be found, inter alia, at www.addgene.org/92170/sequences/.

Techniques for the insertion of transgenes, including large transgenes, capable of expressing functional proteins, including enzymes, cytokines, antibodies, and cell surface receptors are known in the art (see, e.g. Bak and Porteus, Cell Rep. 2017 Jul. 18; 20(3): 750-756 (integration of EGFR); Kanojia et al., Stem Cells. 2015 October; 33(10): 2985-94 (expression of anti-Her2 antibody); Eyquem et al., Nature. 2017 Mar. 2; 543(7643):113-117 (site-specific integration of a CAR); O'Connell et al., 2010 PLoS ONE 5(8): e12009 (expression of human IL-7); Tuszynski et al., Nat Med. 2005 May; 11(5):551-5 (expression of NGF in fibroblasts); Sessa et al., Lancet. 2016 Jul. 30; 388(10043):476-87 (expression of arylsulfatase A in ex vivo gene therapy to treat MLD); Rocca et al., Science Translational Medicine 25 Oct. 2017: Vol. 9, Issue 413, eaaj2347 (expression of frataxin); Bak and Porteus, Cell Reports, Vol. 20, Issue 3, 18 Jul. 2017, Pages 750-756 (integrating large transgene cassettes into a single locus), Dever et al., Nature 17 Nov. 2016: 539, 384-389 (adding tNGFR into hematopoietic stem cells (HSC) and HSPCs to select and enrich for modified cells); each of which is herein incorporated by reference in its entirety.

Homologous Repair Templates

The homologous repair template comprises a polynucleotide encoding a CAR, e.g., a CD19-specific CAR (i.e., a CAR that specifically recognizes CD19 on the surface of cells). In some embodiments, the CAR comprises one or more costimulatory domains. In particular embodiments, a costimulatory domain of the CAR comprises CD28. In particular embodiments, the polynucleotide encodes a CD19-CD28 polypeptide, e.g., CD19.28.ζ-CAR (see, e.g., Eyquem et al. (2017) Nature 543(7643):113-117), the entire disclosure of which is herein incorporated by reference). The polynucleotide comprises a functional coding sequence for the CAR, with optional elements such as promoters or other regulatory elements (e.g., enhancers, repressor domains), introns, WPREs, poly A regions, UTRs (e.g. 3' UTRs). Suitable homologous repair templates for targeting the TRAC locus with a CAR, e.g., a CD19-specific CAR, are described, e.g., in McLeod et al. (2017) Mol. Ther. (25(4): 949-961, and Eyquem et al. (2017) Nature 543(7643):113-117), the entire disclosures of which are herein incorporated by reference.

In some embodiments, the CAR coding sequence in the homologous repair template comprises or is derived from a cDNA for the corresponding gene. In some embodiments, the CAR coding sequence in the homologous repair template comprises the coding sequence from the corresponding gene, e.g., comprising one or more introns. In some embodiments, the transgene in the homologous repair template is codon-optimized, e.g., comprises at least 70%, 75%, 80%, 85%, 90%, 95%, or more homology to the corresponding wild-type coding sequence or cDNA, or a fragment thereof.

In particular embodiments, the template further comprises a polyA sequence or signal, e.g., a bovine growth hormone polyA sequence or a rabbit beta-globin polyA sequence, at the 3' end of the cDNA. In particular embodiments, a Woodchuck Hepatitis Virus Posttranscriptional Regulatory Element (WPRE) is included within the 3'UTR of the template, e.g., between the 3' end of the the coding sequence and the 5' end of the polyA sequence, so as to increase the expression of the transgene. Any suitable WPRE sequence can be used; See, e.g., Zufferey et al. (1999) J. Virol. 73(4):2886-2892; Donello, et al. (1998). J Virol 72: 5085-5092; Loeb, et al. (1999). Hum Gene Ther 10: 2295-2305; the entire disclosures of which are herein incorporated by reference).

To facilitate homologous recombination, the transgene is flanked within the polynucleotide or donor construct by sequences homologous to the target genomic sequence. For example, the transgene can be flanked by sequences surrounding the site of cleavage as defined by the guide RNA. In particular embodiments, the transgene is flanked by sequences homologous to the 3' and to the 5' ends of the TRAC locus, such that the TRAC gene is replaced upon the HDR-mediated integration of the CAR coding sequence, with the result that the endogenous TCR is not expressed. In one such embodiment, the transgene is flanked on one side by a sequence corresponding to the 3' UTR of the TRAC locus, and on the other side by a sequence corresponding to the region of the transcription start site, e.g., just 5' of the start site, of the TRAC gene. The homology regions can be of any size, e.g., 100-1000 bp, 300-800 bp, 400-600 bp, or about 100, 200, 300, 400, 500, 600, 700, 800, 900, 1000, or more bp. In some embodiments, the transgene comprises a promoter, e.g., a constitutive or inducible promoter, such that the promoter drives the expression of the transgene in vivo. In some embodiments, the transgene replaces the coding sequence of TRAC such that its expression is driven by the endogenous TRAC promoter.

Any suitable method can be used to introduce the polynucleotide, or donor construct, into the cell. In some instances, the donor template is single stranded, double stranded, a plasmid or a DNA fragment. In some instances, plasmids comprise elements necessary for replication, including a promoter and optionally a 3' UTR. The vector can be a viral vector, such as a retroviral, lentiviral (both integration competent and integration defective lentiviral vectors), adenoviral, adeno-associated viral or herpes simplex viral vector. Viral vectors may further comprise genes necessary for replication of the viral vector. In particular embodiments, the polynucleotide is introduced using a recombinant adeno-associated viral vector, e.g., rAAV6.

In some embodiments, the targeting construct comprises: (1) a viral vector backbone, e.g. an AAV backbone, to generate virus; (2) arms of homology to the target site of at least 200 bp but ideally at least 400 bp on each side to assure high levels of reproducible targeting to the site (see, Porteus, Annual Review of Pharmacology and Toxicology, Vol. 56:163-190 (2016); which is hereby incorporated by reference in its entirety); (3) a transgene encoding a functional protein and capable of expressing the functional protein, a polyA sequence, and optionally a WPRE element; and optionally (4) an additional marker gene to allow for enrichment and/or monitoring of the modified host cells. Any AAV known in the art can be used. In some embodiments the primary AAV serotype is AAV6. In some embodiments, the vector, e.g., rAAV6 vector, comprising the donor template is from about 1-2 kb, 2-3 kb, 3-4 kb, 4-5 kb, 5-6 kb, 6-7 kb, 7-8 kb, or larger.

In some embodiments, viral vectors, e.g., AAV6 vector, is transduced at a multiplicity of infection (MOI) of, e.g., about $1\times10^3$, $5\times10^3$, $1\times10^4$, $5\times10^4$, $1\times10^5$, between $2\times10^4$ and $1\times10^5$ viruses per cell, or less than $1\times10^5$. In some embodiments, the MOI is about 2000, 2500, 3000, 3500, 4000, 4500, 5000, 5500 vg/cell. In some embodiments, the cells are maintained at a high concentration (>about $5\times10^6$ cells) during transduction for at least about 10, 11, 12 or more hours.

Suitable marker genes are known in the art and include Myc, HA, FLAG, GFP, truncated NGFR, truncated EGFR, truncated CD20, truncated CD19, as well as antibiotic resistance genes. In some embodiments, the homologous repair template and/or vector (e.g., AAV6) comprises an expression cassette comprising a coding sequence for truncated nerve growth factor receptor (tNGFR), operably linked to a promoter such as the Ubiquitin C promoter.

In some embodiments, the donor template or vector comprises a nucleotide sequence homologous to a fragment of the TRAC locus, or a nucleotide sequence is at least 85%, 88%, 90%, 92%, 95%, 98%, or 99% identical to at least 200, 250, 300, 350, 400, 450, 500, or more consecutive nucleotides of the TRAC locus.

The inserted construct can also include other safety switches, such as a standard suicide gene into the locus (e.g. iCasp9) in circumstances where rapid removal of cells might be required due to acute toxicity. The present disclosure provides a robust safety switch so that any engineered cell transplanted into a body can be eliminated, e.g., by removal of an auxotrophic factor. This is especially important if the engineered cell has transformed into a cancerous cell.

The present methods allow for the efficient integration of the donor template at the endogenous TRAC locus. In some embodiments, the present methods allow for the insertion of the donor template in 20%, 25%, 30%, 35%, 40%, 50%, 60%, 70%, 80%, 90% or more cells, e.g., $\alpha\beta$ T cell from an HLA-matched donor. The methods also allow for high levels of expression of the encoded CAR protein in cells, e.g., $\alpha\beta$ T cells from an HLA-matched donor.

The successful integration of the CAR-encoding coding sequence at the TRAC locus can be assessed, e.g., by detecting a loss of TCR on the surface of the cells, and/or a detection of the encoded CAR on the surface of the cells. In some embodiments, at least about 50%, 60%, 70%, 80%, 90%, 95%, or more of the cells show a loss of TCR and/or the presence of the CAR on their surface.

In some embodiments, the ratio of CD4 to CD8 cells among the resulting CAR T cells is from about 0.7:1-1.3:1, or about 0.7:1, 0.8:1, 0.9:1, 1:1, 1.1:1, 1.2:1, or 1.3:1. In particular embodiments, the ratio is about 0.8:1.

The edited CAR T cells can also be assessed in vitro, e.g., to assess their cytotoxic activity against $CD19^+$ target cells, or in vivo using animal models. For example, in some embodiments, the CAR T cells can be co-cultured with, e.g., $CD19^+$ lymphoblastic cells such as Nalm7 or Raji, and the production of cytokines such as IL-2 and/or Interferon-$\gamma$ measured in the supernatant, and/or the loss of CD19+ cells, due to killing by the CAR T cells, counted. The efficacy of the CAR T cells can also be assessed in vivo, e.g., using an Nalm6 xenograft model. For example, $CD19^+$ Nalm6 cells can be i.v. transplanted into mice, e.g., NSG mice, to create a $CD19^+$ leukemia model, and then CAR T cells can be i.v. infused into the mice. In some embodiments, about $5\times10^5$ to $1\times10^7$ CAR T cells are infused, or about $1\times10^6$ to $5\times10^6$. Following the infusion of the CAR T cells, the efficacy and safety of the cells can be assessed, e.g., by examining the leukemia burden, survival, GvHD, etc. in the mice.

5. Administration

Following the integration of the transgene into the genome of the T cells, confirming expression of the encoded CAR protein, and expanding the cells, a plurality of modified T cells can be reintroduced into the subject or patient. In some embodiments, prior to the reintroduction of the T cells, residual cells expressing a TCR (i.e., with an endogenous TCR on the cell surface) are depleted from the cell population. $TCR^+$ cell depletion can be achieved using any of a number of methods, e.g., using magnetic bead activated cell sorting (MACS), e.g., using reagents for which GMP-compatible counterparts are available. In some embodiments, the resulting cell population (i.e., following the depletion step) comprises less than about 1%, 0.5%, 0.1%, 0.05%, 0.04%, 0.03%, $TCR^+\alpha\beta^+$ cells (i.e., fewer than 1%, 0.5%, 0.1%, 0.05%, 0.04%, 0.03%, of the $\alpha\beta$ cells in the population express an endogenous TCR following depletion of the TCR-expressing cells).

The modified host cells of the present disclosure included in the pharmaceutical compositions described above may be administered by any delivery route, systemic delivery or local delivery, which results in a therapeutically effective outcome. These include, but are not limited to, enteral, gastroenteral, epidural, oral, transdermal, intracerebral, intracerebroventricular, epicutaneous, intradermal, subcutaneous, nasal, intravenous, intra-arterial, intramuscular, intracardiac, intraosseous, intrathecal, intraparenchymal, intraperitoneal, intravesical, intravitreal, intracavernous), interstitial, intra-abdominal, intralymphatic, intramedullary, intrapulmonary, intraspinal, intrasynovial, intrathecal, intratubular, parenteral, percutaneous, periarticular, peridural, perineural, periodontal, rectal, soft tissue, and topical. In particular embodiments, the cells are administered intravenously.

Disclosed herein, in some embodiments, are methods of treating a genetic disorder, e.g., leukemia in an individual in need thereof, the method comprising providing to the individual a T cell produced using the genome modification methods disclosed herein. In some instances, the method comprises a modified host αβ T cell isolated from an HLA-matched donor ex vivo, comprising a functional transgene, e.g., CD19-specific CAR transgene, integrated at the TRAC locus, wherein the modified host cell expresses the CAR protein.

Pharmaceutical Compositions

Disclosed herein, in some embodiments, are methods, compositions and kits for use of the modified cells, including pharmaceutical compositions, therapeutic methods, and methods of administration. Although the descriptions of pharmaceutical compositions provided herein are principally directed to pharmaceutical compositions which are suitable for administration to humans, it will be understood by the skilled artisan that such compositions are generally suitable for administration to any animals.

In some embodiments, a pharmaceutical composition comprising a modified donor αβ T cell described herein is provided. The modified donor αβ T cell is genetically engineered to comprise an integrated CAR transgene at the TRAC locus. The modified donor αβ T cell of the disclosure herein may be formulated using one or more excipients to, e.g.: (1) increase stability; (2) alter the biodistribution (e.g., target the cell line to specific tissues or cell types); (3) alter the release profile of an encoded therapeutic factor.

Formulations of the present disclosure can include, without limitation, saline, liposomes, lipid nanoparticles, polymers, peptides, proteins, and combinations thereof. Formulations of the pharmaceutical compositions described herein may be prepared by any method known or hereafter developed in the art of pharmacology. As used herein the term "pharmaceutical composition" refers to compositions including at least one active ingredient (e.g., a modified host cell) and optionally one or more pharmaceutically acceptable excipients. Pharmaceutical compositions of the present disclosure may be sterile.

Relative amounts of the active ingredient (e.g., the modified host cell), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may include between 0.1% and 99% (w/w) of the active ingredient. By way of example, the composition may include between 0.1% and 100%, e.g., between 0.5 and 50%, between 1-30%, between 5-80%, or at least 80% (w/w) active ingredient.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro; Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Injectable formulations may be sterilized, for example, by filtration through a bacterial-retaining filter, and/or by incorporating sterilizing agents in the form of sterile solid compositions which can be dissolved or dispersed in sterile water or other sterile injectable medium prior to use.

Dosing and Administration

In some embodiments, a subject will undergo a conditioning regime before cell transplantation. For example, the conditioning regime may involve administration of cytotoxic agents. The conditioning regime may also include immunosuppression, antibodies, and irradiation. Other possible conditioning regimens include antibody-mediated conditioning (see, e.g., Czechowicz et al., 318(5854) Science 1296-9 (2007); Palchaudari et al., 34(7) Nature Biotechnology 738-745 (2016); Chhabra et al., 10:8(351) Science Translational Medicine 351ra105 (2016)) and CAR T-mediated conditioning (see, e.g., Arai et al., 26(5) Molecular Therapy 1181-1197 (2018); each of which is hereby incorporated by reference in its entirety).

Certain aspects of the present disclosure are directed to methods of providing pharmaceutical compositions including the modified αβ T cell of the present disclosure to target tissues of mammalian subjects, by contacting target tissues with pharmaceutical compositions including the modified host cell under conditions such that they are substantially retained in such target tissues. In some embodiments, pharmaceutical compositions including the modified host cell include one or more cell penetration agents, although "naked" formulations (such as without cell penetration agents or other agents) are also contemplated, with or without pharmaceutically acceptable excipients.

The present disclosure additionally provides methods of administering modified αβ T cells in accordance with the disclosure to a subject in need thereof. The pharmaceutical compositions including the modified αβ T cell, and compositions of the present disclosure may be administered to a subject using any amount and any route of administration effective for preventing, treating, or managing the disorder, e.g., leukemia. The exact amount required will vary from subject to subject, depending on the species, age, and general condition of the subject, the severity of the disease, the particular composition, its mode of administration, its mode of activity, and the like. The subject may be a human, a mammal, or an animal. The specific therapeutically or prophylactically effective dose level for any particular individual will depend upon a variety of factors including the disorder being treated and the severity of the disorder; the activity of the specific payload employed; the specific composition employed; the age, body weight, general health, sex and diet of the patient; the time of administration, route of administration; the duration of the treatment; drugs used in combination or coincidental with the specific modified host cell employed; and like factors well known in the medical arts.

In certain embodiments, modified αβ T cell pharmaceutical compositions in accordance with the present disclosure may be administered at dosage levels sufficient to deliver from, e.g., about $1 \times 10^4$ to $1 \times 10^5$, $1 \times 10^5$ to $1 \times 10^6$, $1 \times 10^6$ to $1 \times 10^7$, or more modified cells to the subject, or any amount sufficient to obtain the desired therapeutic or prophylactic, effect. The desired dosage of the modified host cells of the present disclosure may be administered one time or multiple times. In some embodiments, delivery of the modified host cell to a subject provides a therapeutic effect for at least 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 20 months, 21 months, 22 months, 23 months, 2 years, 3 years, 4 years, 5 years, 6 years, 7 years, 8 years, 9 years, 10 years or more than 10 years.

The modified αβ T cells may be used in combination with one or more other therapeutic, prophylactic, research or diagnostic agents, or medical procedures, either sequentially or concurrently. In general, each agent will be administered at a dose and/or on a time schedule determined for that agent.

Use of a modified mammalian αβ T cell according to the present disclosure for treatment of leukemia or other disorder as described herein is also encompassed by the disclosure.

The present disclosure also contemplates kits comprising compositions or components described herein, e.g., guide RNA (e.g., sgRNA), RNA-guided nuclease (e.g., Cas9), RNPs, i53, and/or homologous templates, as well as, optionally, reagents for, e.g., the introduction of the components into cells. The kits can also comprise one or more containers or vials, as well as instructions for using the compositions in order to modify cells and treat subjects according to the methods described herein.

6. Examples

The present disclosure will be described in greater detail by way of specific examples. The following examples are offered for illustrative purposes only, and are not intended to limit the disclosure in any manner. Those of skill in the art will readily recognize a variety of noncritical parameters which can be changed or modified to yield essentially the same results.

Example 1. Genome Editing of Donor-Derived T Cells to Generate Allogeneic Chimeric Antigen Receptor-Modified T Cells: Optimizing αβ T Cell-Depleted Haploidentical Hematopoietic Stem Cell Transplantation Abstract Allogeneic hematopoietic stem cell transplantation (allo-HSCT) is an effective therapy for high-risk leukemias. In children, graft manipulation based on the selective removal of αβ T cells and B cells (αβ haplo-HSCT) has been shown to reduce the risk of acute and chronic graft-versus-host disease (GvHD), thus expanding the potential allo-HSCT patient population. Leukemic relapse, however, remains a problem. Chimeric antigen receptor T cells (CAR T) can potently eliminate leukemic cells, including in the central nervous system. We hypothesized that by engineering the donor αβ T cells that are removed from the graft by genome editing to express a CD19-specific CAR while simultaneously inactivating the TCR, we could create a therapy that enhances the anti-leukemic efficacy of the stem cell transplant without increasing the risk of GvHD. Using genome editing with Cas9 RNP/rAAV6 delivery, we integrated a CD19-specific CAR in-frame into the TRAC locus. Greater than 90% of cells lost TCR expression, while >75% expressed the CAR. The initial product was further purified with less than 0.05% TCR positive cells remaining. In vitro, the CAR T cells efficiently eliminated target cells and produced high cytokine levels when challenged with CD19-positive leukemia cells. In vivo, the αβTCR⁻CD19 CAR T cells eliminated CD19⁺ tumors in a standard xenograft model without creating xenogenic GvHD. The genome editing process was highly specific with no evidence of off-target insertions or deletions (INDELs). These data support the concept that the addition of αβ TCR⁻CD19 CAR-T cells could enhance the anti-leukemic efficacy of αβ T cell-depleted haploidentical HSCT without increasing the risk of GvHD.

Results

Genome Editing on TCRαβ⁺ Cells that have been Depleted from the Graft During αβhaplo-HSCT to Create CAR T Cells We prospectively collected the TCRαβ⁺/CD19⁺ cell fraction (non-target fraction) removed from grafts during αβ haplo-HSCT procedures. It has recently been shown that HR-mediated genome editing using Cas9 RNP and AAV6 can mediate efficient targeted integration of a CAR into the TRAC locus (36, 37), with up to 50% of cells expressing the CAR. This approach offers the advantages that it establishes TCR knockout in the majority of CAR⁺ cells, avoids the risk for insertional mutagenesis of randomly-integrating viral vectors, and allows the cells to modulate CAR expression if the CAR is integrated in-frame into the endogenous locus (37).

Figure 2A:
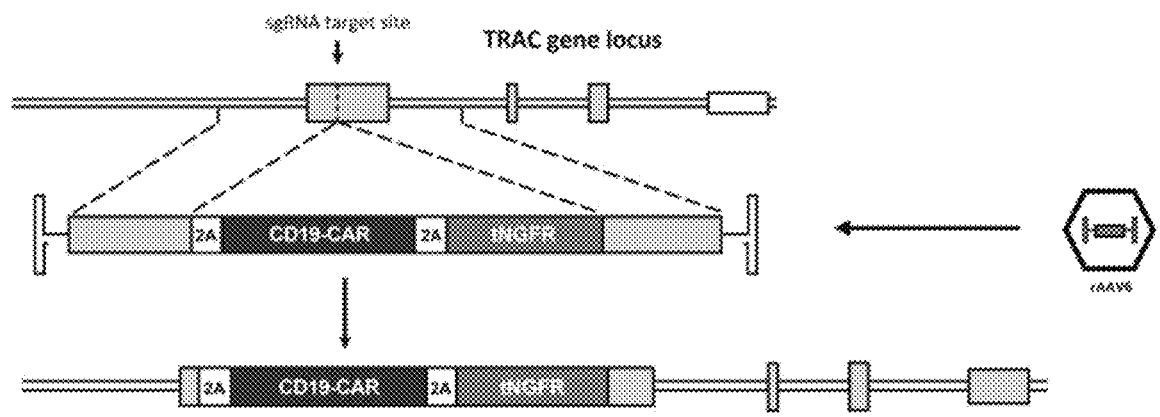
FIGS. 2A-2H. Targeted integration of a CD19-specific CAR into the TRAC locus.

We used homologous recombination-based genome editing (32) to integrate a CD19.28.ζ-CAR in-frame into the open-reading frame of the TRAC locus (FIGS. 1D, 2A), similar to a previously established approach (37). Disruption of TRAC leads to loss of expression of the TCR complex on the cell surface (38). TRAC is advantageous over TRBC because it only exists once per haploid genome. Although 4-1BB co-stimulation has been shown to lead to enhanced persistence of CAR T cells due to decreased exhaustion (39), we chose CD28 as the costimulatory domain in the CAR in order to account for the expected low number of target cells in the setting after HSCT. In the presence of minimal disease burden and absent or low numbers of B cells right after HSCT, the stronger effector signaling from CD28 co-stimulation could lead to enhanced activation and proliferation of the CAR T cells. It was recently shown that the method of targeted integration of a CAR into the TRAC locus with expression from the endogenous promotor can preserve functionality of cells with CD28 co-stimulation (37), which are otherwise prone to exhaustion.

Figures 6A, 6B:
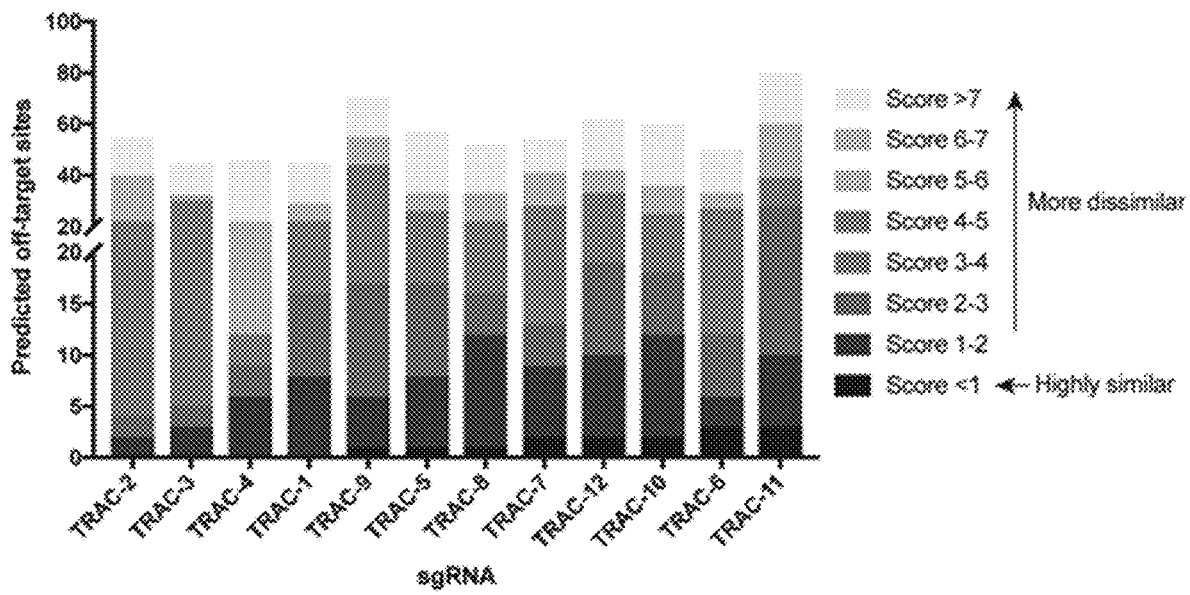
FIGS. 6A-6B. Off-target prediction for sgRNAs at exon 1 of the TRAC locus.

We used an sgRNA (termed TRAC-1) that had previously been shown to have high on-target activity and no detectable off-target activity (40). Potential off-target sites across the human genome were predicted by the COSMID algorithm (34) and comparison to other possible sgRNAs (FIGS. 6A-6B) confirmed that this sgRNA was among the most specific in exon 1 of TRAC with no highly similar off-targets. The most similar predicted off-target site had 3 mismatched nucleotides, suggesting a low probability of Cas9 cleavage activity (see below).

Figure 2B:
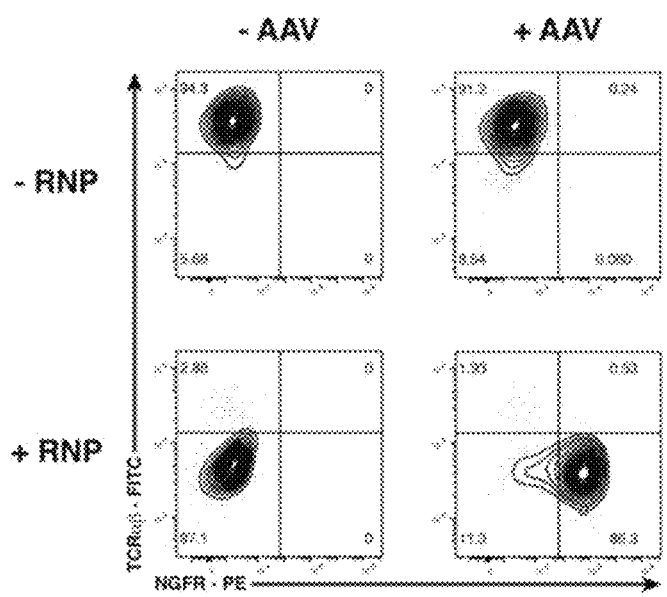
Figure 2C:
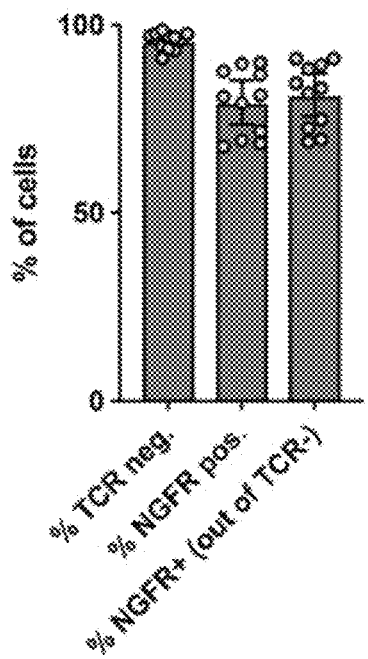
Figure 2D:
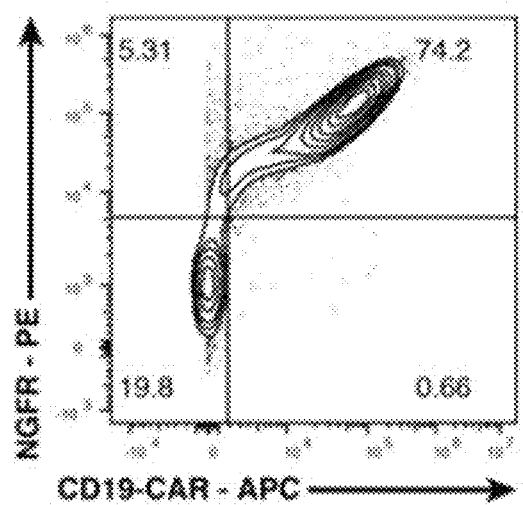

To investigate whether genome editing with TCR knockout and targeted integration of a CAR is feasible in the TCRαβ⁺ T cells that were removed from the graft during αβhaplo HSCT, we cultured and stimulated these cells and electroporated them with a ribonucleoprotein (RNP) complex consisting of a high-fidelity version of the Cas9 protein (41) complexed with chemically-modified sgRNA (42), immediately followed by transduction of a DNA repair template by a non-integrating recombinant adeno-associated virus serotype 6 (rAAV6). Following this process, on average 95.7% of the cells lost TCR expression (95%-CI: 94.2-97.3) and 79.4% (95%-CI: 73.5-85.3) of bulk cells and 81.4% (95%-CI: 75.7-87.1) of TCR cells expressed tNGFR (a truncated non-signaling cell surface form of NGFR which has been used safely in clinical immunotherapy trials) (24) (FIGS. 2B-2C). These unprecedented efficiencies of targeted integration of a large gene expression cassette (2.7 kb) in primary T cells were reproduced in cells from 11 different donors with similar efficiencies (FIG. 2C). Importantly, this proves that cellular double-strand break (DSB) repair can efficiently be skewed toward homologous recombination to the level where it constitutes the predominant repair pathway and targeted integration becomes more frequent than insertion/deletion (InDel)-formation by non-homologous end-joining (NHEJ). Notably, the starting cells had been processed at two different GMP facilities (five at UCSF and six at the Stanford University Laboratory for Cell and Gene Medicine), but the outcome after gene editing was highly reproducible (FIG. 2C). To confirm co-expression of the CAR in the NGFR$^+$ cells, we stained the cells with an antibody that detects the CAR, which confirmed that both genes of the bicistronic expression cassette are translated (FIG. 2D).

Figure 2E:
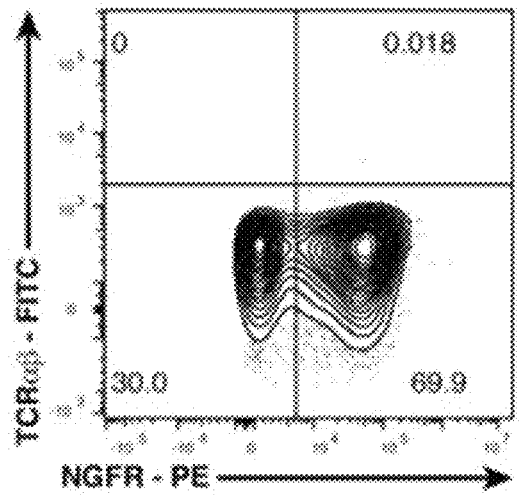
Figure 2F:
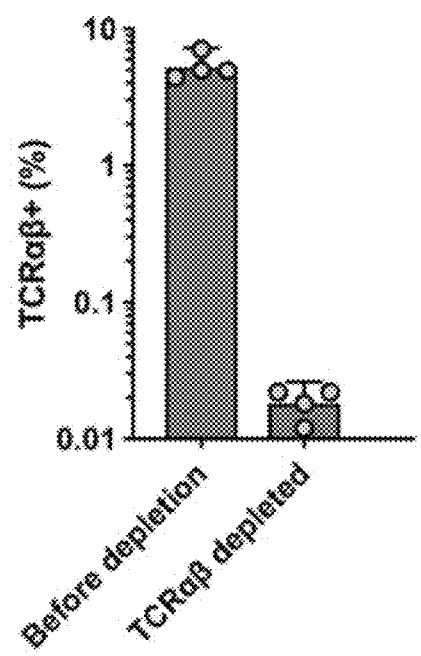

Efficient Depletion of Potentially Alloreactive TCR Cells and Optimization of Editing Methods Despite the efficiency of the genome editing process, a small fraction (<8%) of cells retained expression of their TCR. Prior studies have suggested that the frequency of GvHD occurrence for allogeneic CAR T cells with CD28 costimulation is low (43), supposedly due to exhaustion and clonal depletion of alloreactive cells (44) stimulated through both the CAR and their TCR. Despite these promising results, this is not guaranteed to be universally true, especially since our method creates CAR expression levels different from virally transduced CAR T cells and could lead to different biological properties. The residual TCR$^+$ cells—being HLA haploidentical to the recipient—carry the potential for alloreactivity, and their further depletion from the cell product could decrease the probability of GvHD and allow higher doses of cells to be administered. We therefore evaluated the depletion of residual TCRαβ$^+$ cells from the expanded cell population by magnetic bead activated cell sorting (MACS) using reagents for which GMP-grade counterparts are available. We were able to achieve efficient depletion with a maximum of 0.03% TCRαβ$^+$ cells remaining in the resulting cell product (a depletion efficiency of 2-3 orders of magnitude, FIGS. 2E-2F), a higher efficiency than in prior studies that created TCR-negative CAR T-cells (45, 46). We termed the resulting cell product after genome editing, expansion, and TCRαβ$^+$ depletion "αβTCR$^-$CD29 CAR-T".

Figure 2G:
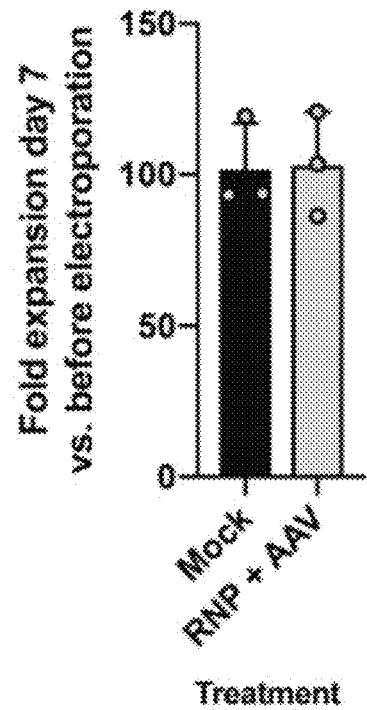
Figure 2H:
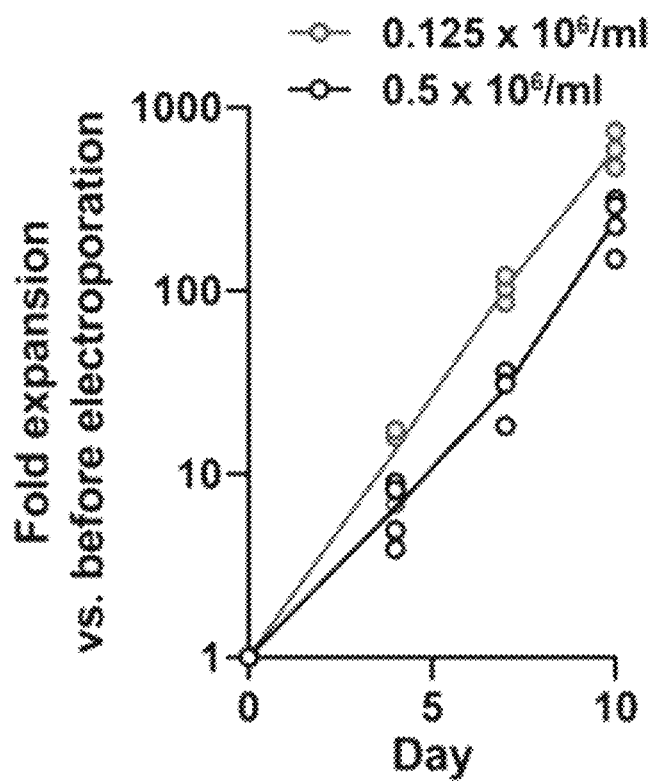
Figure 7A:
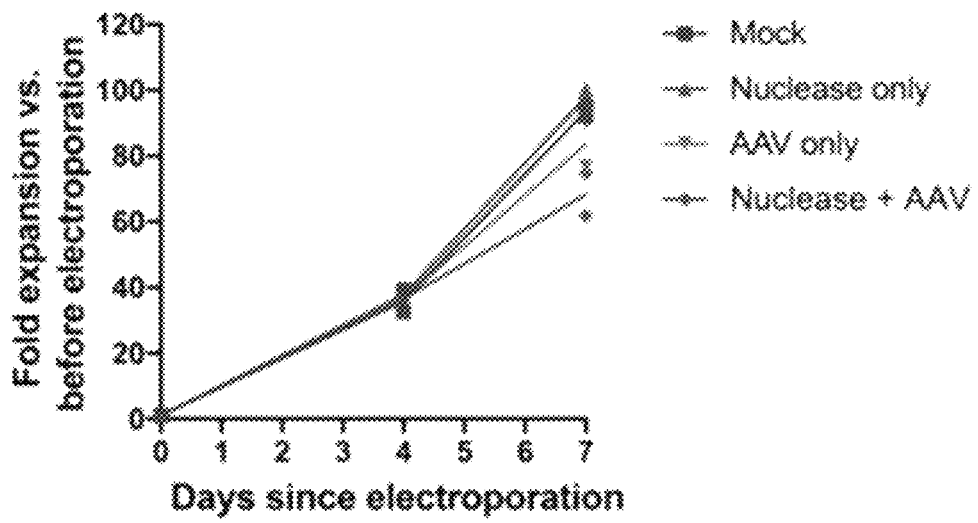
FIGS. 7A-7D. Optimization of T cell targeting conditions and B cell detection.
Figure 7B:
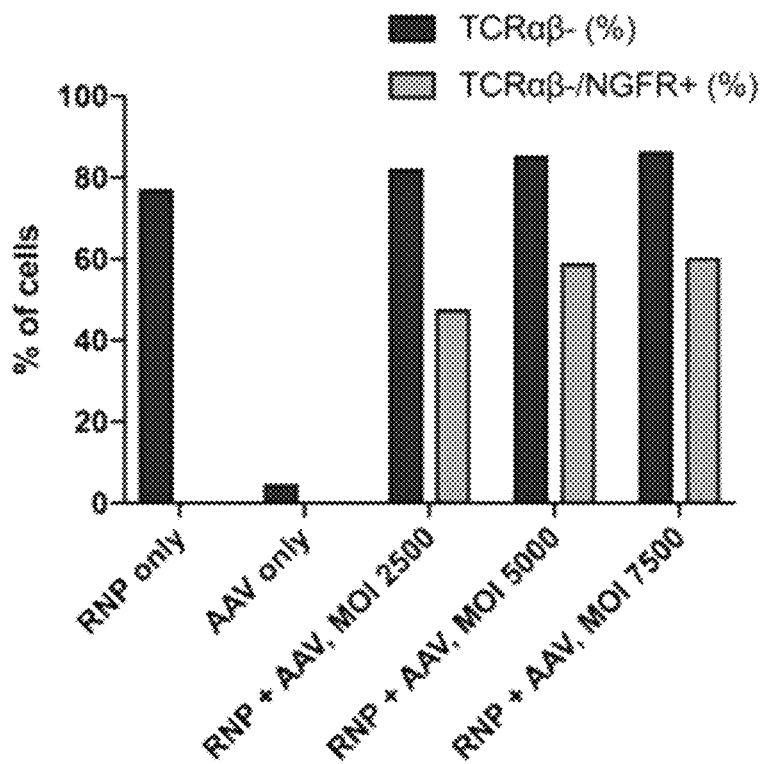
Figure 7C:
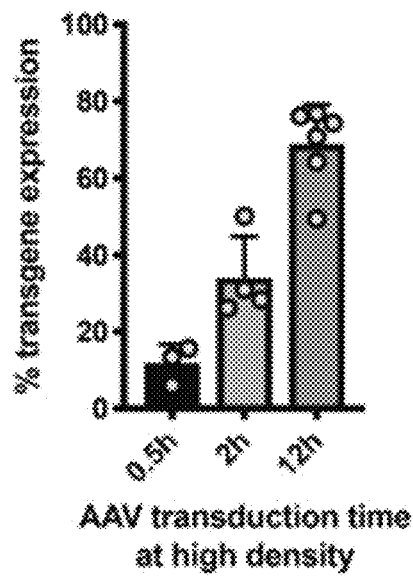

The cells rapidly expanded following genome editing (over 60-fold in 7 days), with no negative effect of RNP electroporation on cell yields, an 11% decrease in expansion after AAV transduction, and a decrease of 27% for cells electroporated with RNP and transduced with AAV (FIG. 7A). This suggested that AAV transduction is the main factor impacting cell expansion, which led us to determine the optimal AAV dose for optimal gene targeting efficiency. Interestingly, we found that a change in the MOI beyond 2500 vg/cell only led to a minor change in targeting outcomes with saturation at 5000 vg/cell (FIG. 7B). Instead, the duration of time during which the cells are kept at a high concentration for AAV transduction (>5×10$^6$ cells per ml) directly after electroporation and before dilution to the target cell density influenced gene targeting outcomes to a greater extent (FIG. 7C). Using an MOI of 5000 vg/cell and a prolonged transduction time at high density (>12 h), we observed that the cells expanded on average 103-fold within the 7 days following gene editing (FIG. 2G). With these conditions for gene editing, the expansion rate of the cells was primarily dependent on the culture density, reaching the threshold of >100-fold expansion in 7 days if cultured at 0.125×10$^6$ cells/ml or within 10 days if cultured at 0.5×10$^6$ cells/ml (FIG. 2I). This confirms that the CAR T cells are able to rapidly expand without further TCR stimulation after gene editing despite the manipulation during the gene editing process. This will aid in the development of a cell product at clinically relevant scale.

To summarize, we achieved efficient disruption of the TCR and high frequencies of CAR expression in T cells derived from the otherwise discarded TCRαβ$^+$ T cells, while allowing for rapid expansion of the resulting cells after the editing process when using an optimized protocol (MOI of 5000 vg/cell with the long AAV transduction time).

Phenotype and In Vitro Efficacy

Figure 3A:
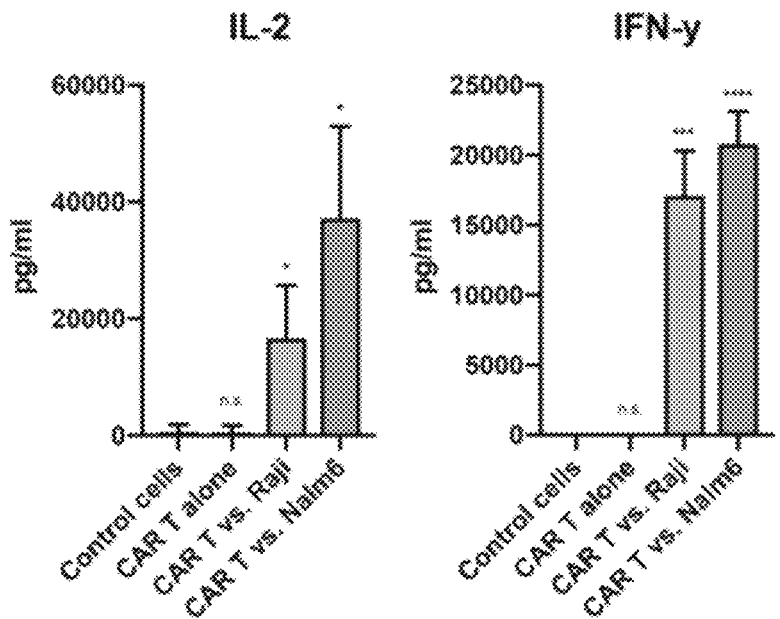
FIGS. 3A-3G. In vitro functionality of CAR T cells engineered from TCRαβ+ cells.
Figure 3B:
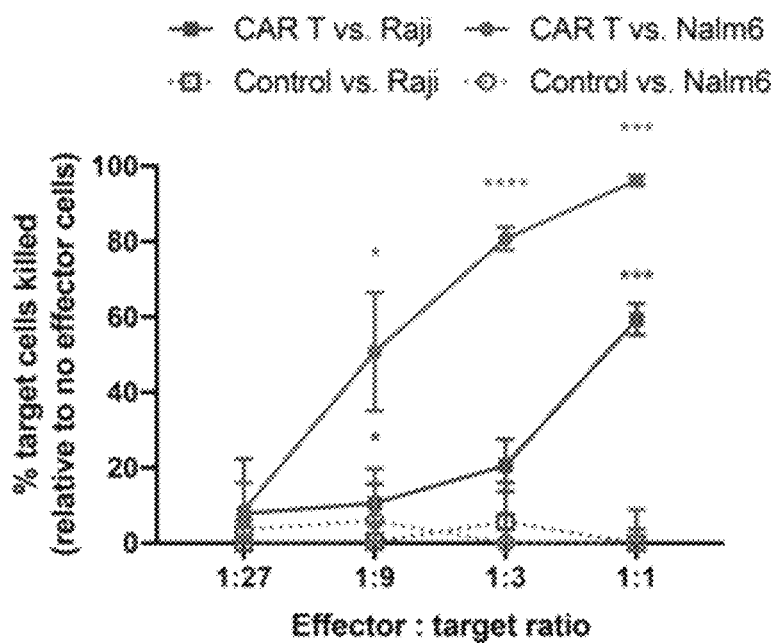

To determine in vitro cytotoxic activity and cytokine production, we used the CD19$^+$ lymphoblastic cell lines Nalm6-GL and Raji (GFP-Luciferase transduced) as target cells. After co-culture for 20 hours, we were able to measure production of IL-2 and Interferon-γ in the cell culture supernatant, specifically for cells with targeted integration of the CAR (FIG. 3A). To estimate the fraction of target cells that was killed, we determined the counts of target cells (identified by their GFP expression) after 20 hours of co-culture with either CAR T cells or control cells relative to samples cultured without effector cells, which showed cytotoxic activity even at low effector:target (E:T) ratios (FIG. 3B).

Figure 3C:
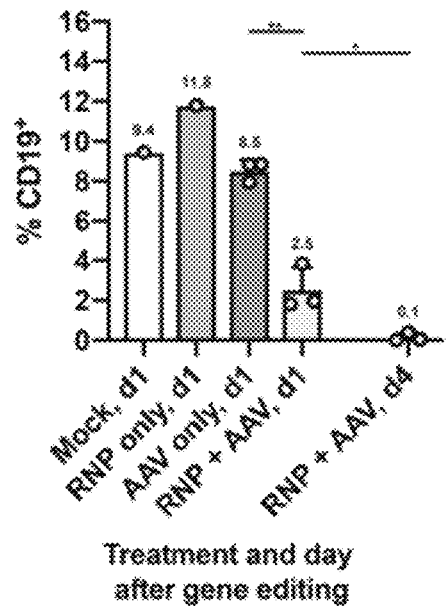
Figure 7D:
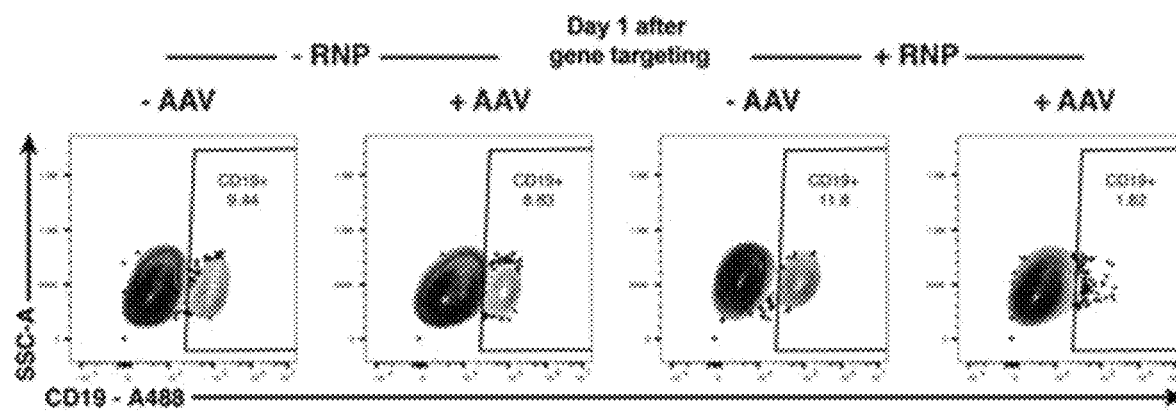

To determine the fate of the B cells, which are part of the source cell population besides the αβ T cells, we followed the CD19$^+$ cell population by phenotyping and were able to detect their disappearance as early as 24 hours after gene targeting (2.53% vs 7.9-11.8% in the control populations in which the T cells do not express CAR), suggesting early cytotoxic activity of CD19-specific CAR cells (FIGS. 3C, 7D). Follow-up showed that the cell product continues to self-deplete from the residual B cells over time (FIG. 3C). The presence of CD19$^+$ cells in the manufacturing process may be the stimulus for the excellent T cell expansion we observe in the TCR$^-$ cells during the manufacturing process.

Figure 3D:
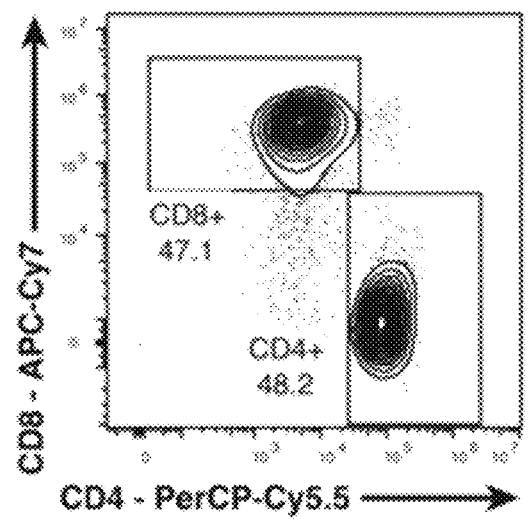
Figure 3E:
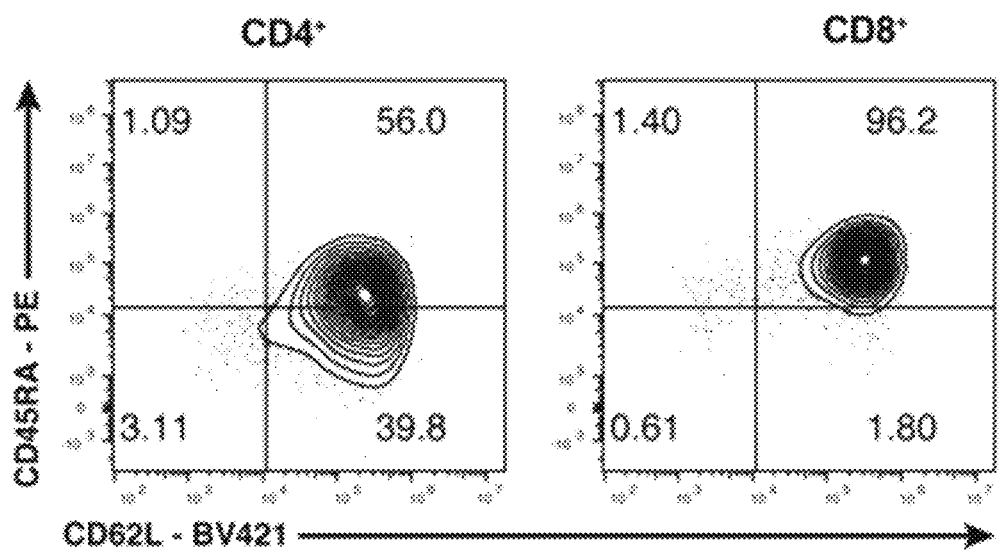
Figure 3F:
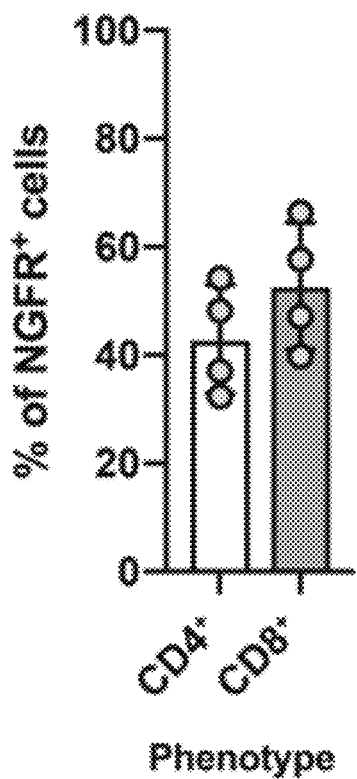
Figure 3G:
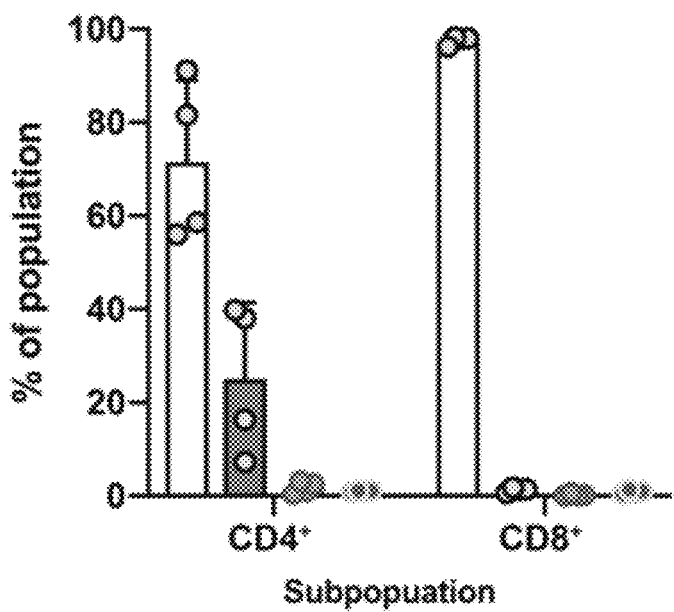

We next performed phenotyping of the resulting CAR T cells after the editing process and found that the ratio of CD4 to CD8 cells in the resulting CAR T cell product is about 0.8:1 (FIGS. 3D, 3F). The majority of CD4$^+$ were of naïve and central memory (CM) phenotype, while in the CD8$^+$ subpopulation the majority of cells showed a naïve phenotype (FIGS. 3E, 3G). This confirms that the CAR T cells have a balanced CD4:CD8 ratio, and that despite the TCR stimulation before genome editing and the transient activation through the CAR mediated by the B cell cytotoxicity, both subpopulations have a high fraction of naïve and CM cells.

Antileukemic Efficacy In Vivo

Figure 4A:
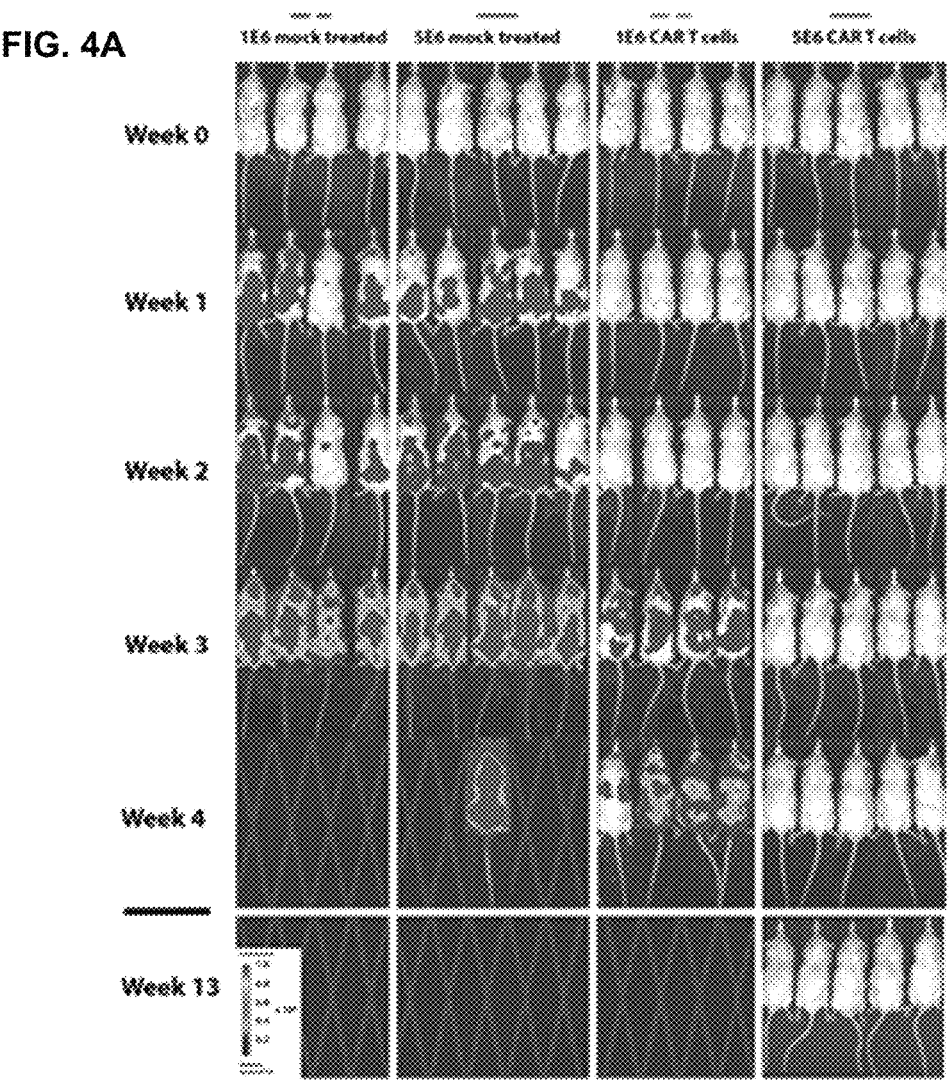
FIGS. 4A-4B. Antileukemic activity of genome edited CAR T cells in vivo.
Figure 4B:
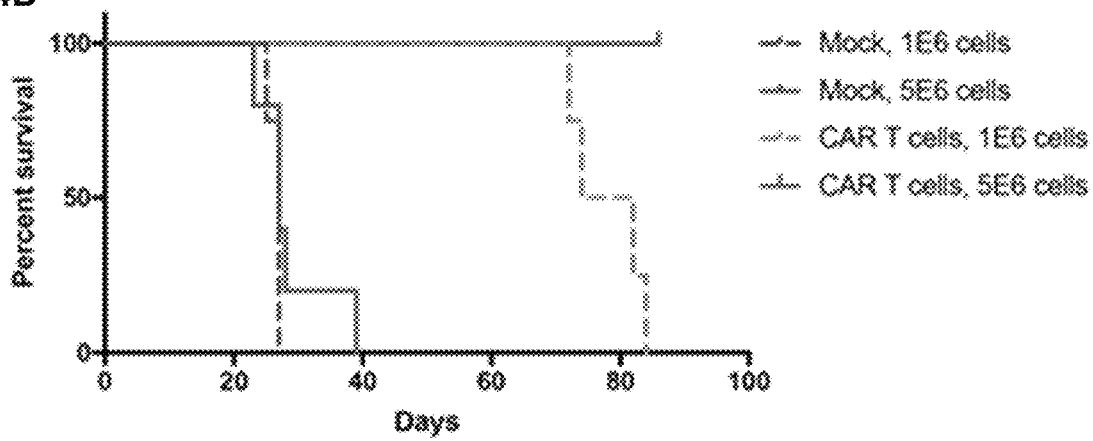
Figure 8A:
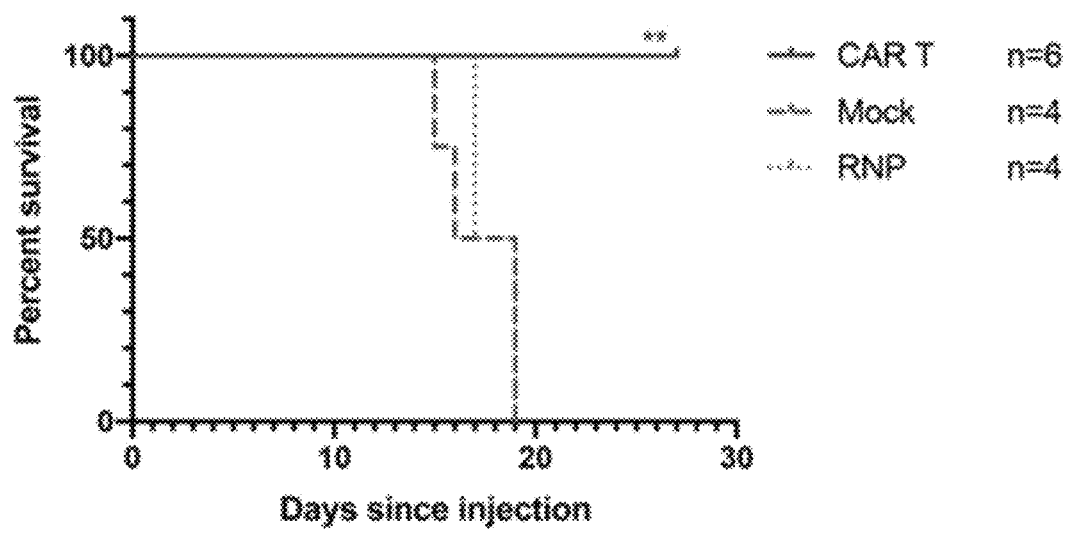
FIGS. 8A-8B: CAR T cell efficacy in vivo using two different control groups.
Figure 8B:

We determined the activity of the αβTCR$^-$CD19 CAR-T product in vivo using a standard Nalm6 xenograft model (47). We transplanted 5×10$^5$ CD19$^+$ Nalm6 cells i.v. into NSG mice to create the CD19+ leukemia model. Four days later we i.v. infused $1 \times 10^6$, $5 \times 10^6$ αβTCR−CD19 CAR-T or control cells and followed leukemia burden by bioluminescence imaging. The higher dose of CAR T cells led to a rapid and complete eradication of leukemia that was durable for at least 3 months, while the lower dose led to a transient decrease in leukemia burden and improved survival, although the mice eventually relapsed (FIG. 4A). While control mice became moribund and died from disease within 4 weeks, life was significantly extended at both doses of CAR T cells (FIG. 4B, log-rank test: $p<0.01$ for $5 \times 10^6$ cells, $p<0.05$ for $1 \times 10^6$ cells). No xenogeneic GvHD was observed in any of the mice, demonstrating low GvHD potential in the T cell products. We repeated the experiment at the CAR T dose level of $5 \times 10^6$ cells per mouse using two different control groups, either mock-treated T cells (expressing their endogenous TCR) or RNP-treated T cells (TCR knockout), which confirmed comparable T cell efficacy and showed no difference between these control groups (FIGS. 8A, 8B).

Off-Target Evaluation

Figure 5B:
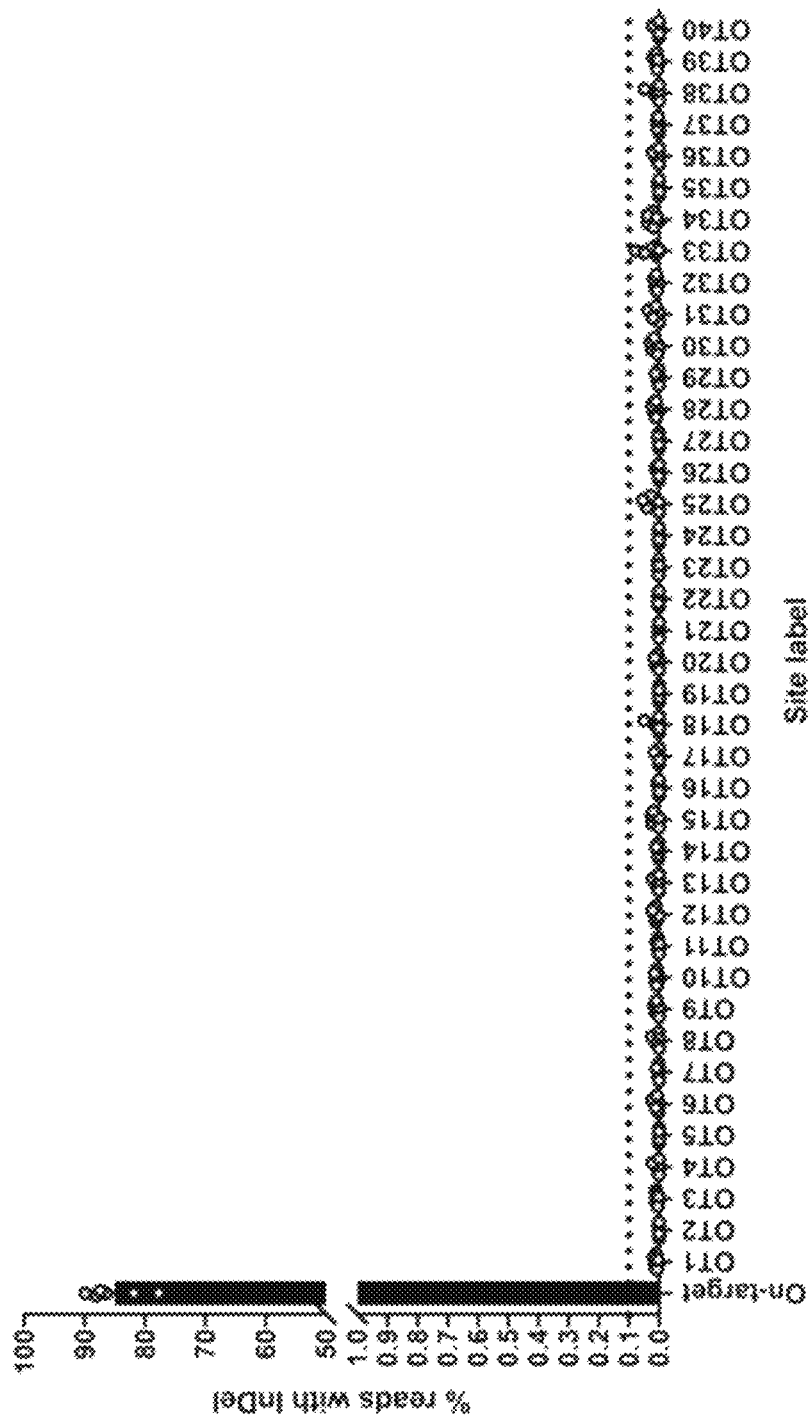

While the gRNA has previously been evaluated in an IDLV capture assay (40), we extended the specificity analysis to measure the off-target activity of the TRAC-targeting RNP using targeted next generation sequencing. We created a list of predicted off-target sites determined by the COSMID online tool (FIG. 5A) and performed targeted deep sequencing of the sites in T cells from 6 different donors electroporated with the RNP (or mock electroporated to determine background). Sequencing confirmed the specificity of the endonuclease with high activity at the on-target site, but no detectable INDELs at off-target sites above the detection limit of 0.1% in any of the samples (FIG. 5B).

Discussion

In the case of persistent MRD after HSCT, relapse risk is high, but treatment options are limited during the time of engraftment and immune recovery. Many immune-based therapies are futile in this period as the immune system is only slowly developing, and transplant protocols typically include immune suppression which would inhibit any adoptive cell-based therapy like CAR T cells. αβ haplo-HSCT represents an excellent platform for adoptive immunotherapy because not only does it help overcome the limited availability of HLA-matched donors, but post-HSCT immunosuppression is not required. It has shown robust clinical results in pediatric patients (8), but a fraction of patients still relapses.

We here hypothesize that a donor-derived CAR T cell product with TCR knockout after haplo-HSCT has the potential to dissociate the beneficial antileukemic activity from harmful GvHD, which are inherently connected to each other when infusing unmanipulated donor-derived lymphocytes (DLI). This would take advantage of both the GvL-effect of allo-HSCT and the antileukemic activity of CAR T cells. It will also supplement the polyclonal, HLA-dependent immune response that the transplanted immune system elicits after HSCT with the antigen-specific, HLA-independent cytotoxicity of CAR T cells, in order to address relapses after allogeneic HSCT that occur due to downregulation of HLA molecules (48-50). Moreover, manufacturing CAR T cells from the donor would maintain immune tolerance between the CAR T product and donor immune system (which are HLA identical) while taking advantage of the beneficial features of healthy donor T cells.

Our innovative approach avoids the risk of manufacturing failures that comes with the use of autologous T cells, but is distinct from allogeneic, "off-the-shelf" CAR T cells, as it creates a personalized CAR T cell product for every patient from the respective haploidentical donor. It will therefore not benefit from the same cost-effectiveness that "off-the-shelf" CAR T cells promise, which aim to reduce prices by manufacturing doses for multiple patients during a single run. On the other hand, creating αβTCR−CD19 CAR-T from the left-over cell fraction and administering them after HSCT will be more economical than the common practice of following the administration of autologous CAR T cells with allogeneic HSCT(51), which carries the high price tag of current CAR T cell products but then results in their eradication by the donor immune system. Our proposed protocol, in contrast, allows for increased CAR T cell persistence, since the cells are HLA-identical to the immune system after HSCT. This could create prolonged antileukemic surveillance from a single cell dose, or alternatively enable administration of multiple CAR T cell doses for the same patient created from one manufacturing run. Moreover, the cells would benefit from the lymphopenia after HSCT, enabling their engraftment and prolonged activity without additional lymphodepleting therapy. Importantly, our approach allows for the creation of both the product containing the hematopoietic stem cells and the gene edited CAR T cells from a single apheresis, as the CAR T cells are made from the otherwise discarded cell fraction. This avoids an additional procedure and thereby leads to cost reduction and mitigates the risks and discomfort for the donor. This will be of particular importance when very young persons are the HSCT donors, e.g., younger siblings of pediatric patients, or the children of adult patients.

Clinical trials have shown that CAR T cells lead to increased survival if disease burden is low before their administration (52), and that high disease burden (53) is associated with an increased risk of side effects like cytokine release syndrome (CRS). A potential advantage of using CAR T cells after HSCT is therefore the diminished leukemia burden due to the conditioning regimen and the transplant, which might translate to improved outcomes of the CAR T treatment and a lower CRS incidence, but in the absence of informative animal models this needs to be tested in a clinical trial.

An alternative haploidentical HSCT approach using post-transplant cyclophosphamide (pT-Cy) for in-vivo T cell depletion has shown promising results, though published work, to date, has focused primarily on adults (54,55). Although the use of αβ haplo-HSCT requires a specific manufacturing expertise and upfront costs to establish the graft processing, we believe that the absence of post-HSCT pharmacological GvHD prophylaxis, the very low rate of severe GvHD and the low infection rate render this approach ideal for the combination with post-HSCT adoptive immunotherapy. Eventually, it will need to be determined in prospective trials comparing αβ haplo-HSCT and pT-Cy in children which alternative represents the optimal treatment under which circumstances.

CAR T cells from healthy, allogeneic donors—which have preserved T cell numbers and functionality and promise to overcome the manufacturing challenges and product variability of autologous CAR T cells (29, 56-59)—carry the potential to mediate GVHD if they still carry their endogenous TCR60. Only a limited number of patients have been treated with allogeneic CAR T cells but the frequency of GvHD has been surprisingly low when a co-stimulatory domain derived from the CD28 molecule was used in the CAR construct43, which raises the question whether TCR deletion is necessary. Mechanistic studies suggest that the simultaneous activation of both the CD28-costimulated CAR and the TCR can lead to exhaustion and clonal deletion of alloreactive cells (44). The selective deletion of alloreactive T cells in this mode occurred, however, only at certain ratios between CAR T cells and target cells, and an excess of CAR T cells was able to induce GvHD (44). Furthermore, most CAR T cell products are transfused without selection of the transduced cells and therefore contain untransduced cells not expressing a CAR that retain their alloreactive potential. Removal of the TCR from the cell surface, e.g. by genome editing approaches (37, 38, 46), is the best approach to reduce the risk of GvHD of allogeneic cells and additionally might prevent the induction of T cell dysfunction that can develop if the CAR and TCR are engaged on the same cell (61). CAR T cells with genome editing-based disruption of the TCR are currently being explored in clinical trials (62).

Although CAR T cells with TCR knockout are often referred to as "universal" cells, they can still be rejected by the host immune system as it recovers from the immunodepletion given prior to CAR T infusion (63). Additional genetic engineering has been proposed to prevent recognition by the host immune system, e.g., the use of genome editing to remove HLA class 1 expression (64,65) and the expression of molecules that suppress NK cell activity (66). These strategies raise the issue that if they succeed to completely avoid recognition and clearance by the host immune system, the cells also escape immune surveillance in case they become infected with viruses or turn malignant. Therefore, engineering an allogeneic CAR T cell graft that achieves bi-directional immune tolerance with a host immune system including satisfactory immune surveillance remains an unresolved challenge. The use of donor-derived T cells to create a TCR⁻ CAR T cell product that is administered after allogeneic HSCT enables HLA compatibility of the CAR T cells with the donor-derived host immune system after immune reconstitution. A remaining limitation to full immune compatibility is the nature or the CAR that we used, which is a synthetic protein with non-human parts and potential immunogenicity. Fully humanized CARs are currently in early stages of clinical trials (67). It is possible that in the post-transplant setting the development of an immune response to the CAR will not occur but that can only be tested in a human clinical trial.

It has previously been shown that transfusion of $10^4$ T cells per kg can mediate rapid and protective immune reconstitution (68), while among a cohort of 98 patients undergoing αβ haplo-HSCT that received a median of $4 \times 10^4$ TCRαβ⁺ cells, no patient developed high-grade acute and only 1 out of 98 patients developed extensive chronic GvHD (8). With the efficient depletion of TCRαβ⁺ cells that we demonstrated, we estimate that therapeutically relevant doses of the cell product (theoretically up to $33 \times 10^6$ cells/kg) can be infused without administering more than $10^4$ TCR⁺ cells per kg. It remains to be evaluated in a clinical trial whether the small number of αβ T cells that are transfused with the HSC fraction, together with the residual TCR⁺ cells in the CAR T cell product, substantially increase the GvHD risk.

In conclusion, we here establish a preclinical proof-of-concept for using the non-target fraction that is normally discarded during the αβ⁺ T cell/CD19⁺ B cell depletion to engineer a CD19-specific CAR T cell product with low risk of causing GvHD. αβ haplo-HSCT combined with graft-derived αβTCR⁻CD19 CAR-T cells represents an appealing contribution that makes it possible to: 1) identify a donor virtually for every patient in need, 2) overcome the issues related to manufacturing autologous CAR T cells, 3) abrogate the risk of GvHD through genome editing of the TRAC locus, and 4) provide a persistent targeted immune surveillance after HSCT. Furthermore, the use of adoptive post-HSCT immunotherapy can potentially translate in the future into desirable conditioning regimens with lower toxicity and better preservation of fertility.

Methods

Plasmid Cloning and AAV Production

Transfer plasmids were cloned between the ITRs in pAAV-MCS (Agilent Technologies). The CAR comprises a GM-CSFRα leader sequence, the FMC63 scFv (31), CD28 hinge, transmembrane and intracellular sequences and the CD3ζ intracellular domain. rAAV6 was produced as previously described (32) or acquired from Vigene Biosciences Inc. The absolute concentration of ITR copy numbers was determined by droplet digital PCR (Bio-rad) using previously reported primer and probe sets (33).

Apheresis and Cell Processing

αβhaplo-HSCT donors received granulocyte-colony stimulating factor (G-CSF) for 4 days at the total dose of 16 μg/kg body weight and apheresis was performed on the 5th day. When on day 4 the CD34⁺ cell count was <40/μL, a CXCR4 antagonist (Plerixafor, Mozobil) was given. Manipulations were performed in a closed system according to GMP standards with clinical grade reagents and instrumentation from Miltenyi Biotec (Bergisch Gladbach, Germany).

T Cell Culture and Genome Editing

The TCRαβ⁺/CD19⁺ cell fraction (non-target fraction from the graft manipulation procedure) was used fresh or cryopreserved. T cells were activated for 3 days and beads removed before electroporation. Electroporation and gene targeting were performed as previously described (32).

MACS Depletion

To deplete residual TCRαβ⁺ cells, cells were pooled, washed and stained with anti-TCRαβ-Biotin (Miltenyi). The secondary labelling was performed with Streptavidin-conjugated microbeads (Miltenyi). After the incubation time, the cells were diluted at least 1:10 with FACS buffer and directly passed through a pre-equilibrated LD column (Miltenyi) in a magnetic field. The column was washed twice and the flow-through harvested, washed and resuspended in medium.

In Vitro Cytokine Measurement and Cytotoxicity Assay

CD19⁺ Nalm6-GL cells were used in co-culture assays with the CAR T cells or control T cells to determine IL-2 and IFN-γ production of the CAR T cells and cytotoxicity. For additional details see Example 2.

In Vivo Xenograft Assay $5 \times 10^5$ CD19⁺ Nalm6-GL cells were transplanted i.v. into 6-12 week old male NSG mice. 4 days later, tumor burden was evaluated by IVIS bioluminescence imaging (PerkinElmer) and CAR T cells or control cells injected i.v. at the cell count indicated. Tumor burden was followed up weekly by IVIS imaging.

Antibodies Used for Flow Cytometry

NGFR-APC, NGFR-PE, TCRαβ-FITC, CD19-A488, CD19-A700, CD62L-BV421, CD45RA-PE, CD4-PerCP-Cy5.5, CD8a-APC-Cy7 (all Biolegend). For CD45RA/CD62L staining, isotype controls as recommended by the manufacturer were used to determine positive and negative populations.

Off-Target Analysis sgRNA target sites in the target region were identified and their specificity score calculated by bioinformatics (crispor.tefor.net) (3. COSMID (crispr.bme.gatech.edu) (34) was used to identify potential off-target sites in the human genome. For analysis of predicted off-targets, gene editing or mock treatment was performed on T cells from 6 different donors and all predicted off-target sites sequenced using an Illumina MiSeq as described previously (35). For additional details see Example 2.

Statistics

Plots show means with error bars representing either standard deviation or the 95% confidence interval (CI), as indicated. Groups were compared by statistical tests as indicated in figure legends using Prism 7 (GraphPad). Asterisks indicate statistical significance: *=p<0.05, =p<0.01, *=p<0.001, ****=p<0.0001. All t tests are two-tailed.

Abbreviations

αβ haplo-HSCT TCR αβ$^+$/CD19$^+$-depleted hematopoietic stem cell transplantation
CAR Chimeric antigen receptor
CI Confidence interval
CM Central memory
CR Complete remission
CRS Cytokine-release syndrome
DLI Donor lymphocyte infusion
DSB Double-strand break
EM Effector memory
FLuc Firefly luciferase
GvHD Graft-versus-host disease
GvL Graft-versus-leukemia
HLA Human leukocyte antigen
HR Homologous recombination
HSCT Hematopoietic stem cell transplantation
HSPC Hematopoietic stem and progenitor cells
HSV-TK Herpes simplex virus thymidine kinase
iCasp9 Inducible caspase 9
INDEL Insertion or deletion
MACS Magnetic bead activated cell sorting
MOI Multiplicity of infection
MRD Minimal residual disease
NHEJ Non-homologous end joining
NRM Non-relapse mortality
ORF Open reading frame
rAAV6 Recombinant adeno-associated virus serotype 6
RNP Ribonucleoprotein
TCR T cell receptor
tNGFR Truncated version of the nerve growth factor receptor
vg Vector genomes

REFERENCES

1. Schrappe M, Hunger S P, Pui C-H, et al. Outcomes after Induction Failure in Childhood Acute Lymphoblastic Leukemia. N Engl J Med 2012; 366(15):1371-1381.
2. Balduzzi A, Valsecchi M G, Uderzo C, et al. Chemotherapy versus allogeneic transplantation for very-high-risk childhood acute lymphoblastic leukaemia in first complete remission: comparison by genetic randomisation in an international prospective study. Lancet 2005; 366(9486):635-642.
3. Peters C, Schrappe M, von Stackelberg A, et al. Stem-Cell Transplantation in Children With Acute Lymphoblastic Leukemia: A Prospective International Multicenter Trial Comparing Sibling Donors With Matched Unrelated Donors—The ALL-SCT-BFM-2003 Trial. J Clin Oncol 2015; 33(11):1265-1274.
4. Horowitz M M, Gale R P, Sondel P M, et al. Graft-versus-leukemia reactions after bone marrow transplantation. Blood 1990; 75(3):555-62.
5. Weiden P L, Flournoy N, Thomas E D, et al. Antileukemic Effect of Graft-versus-Host Disease in Human Recipients of Allogeneic-Marrow Grafts. N Engl J Med 1979; 300(19):1068-1073.
6. Gragert L, Eapen M, Williams E, et al. HLA Match Likelihoods for Hematopoietic Stem-Cell Grafts in the U.S. Registry. N Engl J Med 2014; 371(4):339-348.
7. Chaleff S, Otto M, Barfield R C, et al. A large-scale method for the selective depletion of alphabeta T lymphocytes from PBSC for allogeneic transplantation. Cytotherapy 2007; 9(8):746-754.
8. Bertaina A, Zecca M, Buldini B, et al. Unrelated donor vs HLA-haploidentical alpha/beta T-cell and B-cell depleted HSCT in children with acute leukemia. Blood 2018; 132(24):2594-2607.
9. Lang P, Feuchtinger T, Teltschik H-M, et al. Improved immune recovery after transplantation of TCR/CD19-depleted allografts from haploidentical donors in pediatric patients. Bone Marrow Transplant 2015; 50(52):S6-S10.
10. Locatelli F, Merli P, Pagliara D, et al. Outcome of children with acute leukemia given HLA-haploidentical HSCT after T-cell and B-cell depletion. Blood 2017; 130(5):677-685.
11. Locatelli F, Bauquet A, Palumbo G, Moretta F, Bertaina A. Negative depletion of α/+ T cells and of CD19+B lymphocytes: A novel frontier to optimize the effect of innate immunity in HLA-mismatched hematopoietic stem cell transplantation. Immunol Lett 2013; 155(1-2):21-23.
12. Locatelli F, Pende D, Mingari M C, et al. Cellular and molecular basis of haploidentical hematopoietic stem cell transplantation in the successful treatment of high-risk leukemias: Role of alloreactive NK cells. Front Immunol 2013; 4:15.
13. de Witte M A, Kuball J, Miller J S. NK Cells and T Cells for Relapse Protection after Allogeneic Hematopoietic Cell Transplantation (HCT). Curr Stem Cell Reports 2017; 3(4):301-311.
14. Klingebiel T, Cornish J, Labopin M, et al. Results and factors influencing outcome after fully haploidentical hematopoietic stem cell transplantation in children with very high-risk acute lymphoblastic leukemia: impact of center size: an analysis on behalf of the Acute Leukemia and Pediatric Disease Working Parties of the European Blood and Marrow Transplant group. Blood 2010; 115(17):3437-3446.
15. Kongtim P, Lee D A, Cooper L J N, Kebriaei P, Champlin R E, Ciurea S O. Haploidentical Hematopoietic Stem Cell Transplantation as Platform for Post-transplant Cellular Therapy. Biol Blood Marrow Transplant 2015; 21(10):1714.
16. Lutz C, Massenkeil G, Nagy M, et al. A pilot study of prophylactic donor lymphocyte infusions to prevent relapse in adult acute lymphoblastic leukemias after allogeneic hematopoietic stem cell transplantation. Bone Marrow Transplant 2008; 41(9):805-812.
17. Liga M, Triantafyllou E, Tiniakou M, et al. High Alloreactivity of Low-Dose Prophylactic Donor Lymphocyte Infusion in Patients with Acute Leukemia Undergoing Allogeneic Hematopoietic Cell Transplantation with an Alemtuzumab-Containing Conditioning Regimen. Biol Blood Marrow Transplant 2013; 19(1):75-81.
18. Bader P, Klingebiel T, Schaudt A, et al. Prevention of relapse in pediatric patients with acute leukemias and MDS after allogeneic SCT by early immunotherapy initiated on the basis of increasing mixed chimerism: a single center experience of 12 children. Leukemia 1999; 13(12):2079-86.

19. Dominietto A, Pozzi S, Miglino M, et al. Donor lymphocyte infusions for the treatment of minimal residual disease in acute leukemia. Blood 2007; 109(11):5063-4.
20. Lankester A C, Bierings M B, van Wering E R, et al. Preemptive alloimmune intervention in high-risk pediatric acute lymphoblastic leukemia patients guided by minimal residual disease level before stem cell transplantation. Leukemia 2010; 24(8):1462-1469.
21. Willasch A M, Salzmann-Manrique E, Krenn T, et al. Treatment of relapse after allogeneic stem cell transplantation in children and adolescents with ALL: the Frankfurt experience. Bone Marrow Transplant 2017; 52(2):201-208.
22. Anandi P, Tian X, Ito S, et al. Ex vivo T-cell-depleted allogeneic stem cell transplantation for hematologic malignancies: The search for an optimum transplant T-cell dose and T-cell add-back strategy. Cytotherapy 2017; 19(6):735-743.
23. Di Stasi A, Tey S-K, Dotti G, et al. Inducible Apoptosis as a Safety Switch for Adoptive Cell Therapy. N Engl J Med 2011; 3651673-1683.
24. Bonini C, Ferrari G, Verzeletti S, et al. HSV-TK gene transfer into donor lymphocytes for control of allogeneic graft-versus-leukemia. Science 1997; 276(5319):1719-24.
25. Locatelli F, Ruggeri A, Merli P, et al. Administration of BPX-501 Cells Following A T and B-Cell-Depleted HLA Haploidentical HSCT (haplo-HSCT) in Children with Acute Leukemias. Blood 2018; 132(Suppl 1):abstract 307.
26. Majzner R G, Heitzeneder S, Mackall C L. Harnessing the Immunotherapy Revolution for the Treatment of Childhood Cancers. Cancer Cell 2017; 31(4):476-485.
27. Rivière I, Sadelain M. Chimeric Antigen Receptors: A Cell and Gene Therapy Perspective. Mol Ther 2017; 25(5):1117-1124.
28. Sadelain M. CD19 CAR T Cells. Cell 2017; 171(7):1471.
29. Ruella M, Xu J, Barrett D M, et al. Induction of resistance to chimeric antigen receptor T cell therapy by transduction of a single leukemic B cell. Nat Med 2018; 24(10):1499-1503.
30. Fraietta J A, Nobles C L, Sammons M A, et al. Disruption of TET2 promotes the therapeutic efficacy of CD19-targeted T cells. Nature 2018; 558(7709):307-312.
31. Nicholson I C, Lenton K A, Little D J, et al. Construction and characterisation of a functional CD19 specific single chain Fv fragment for immunotherapy of B lineage leukaemia and lymphoma. Mol Immunol; 34(16-17):1157-65.
32. Bak R O, Dever D P, Porteus M H. CRISPR/Cas9 genome editing in human hematopoietic stem cells. Nat Protoc 2018; 13(2):358-376.
33. Haeussler M, Schonig K, Eckert H, et al. Evaluation of off-target and on-target scoring algorithms and integration into the guide RNA selection tool CRISPOR. Genome Biol 2016; 17(1):148.
34. Cradick T J, Qiu P, Lee C M, Fine E J, Bao G. COSMID: A Web-based Tool for Identifying and Validating CRISPR/Cas Off-target Sites. Mol Ther—Nucleic Acids 2014; 3e214.
35 Lee C M, Cradick T J, Bao G. The *Neisseria meningitidis* CRISPR-Cas9 System Enables Specific Genome Editing in Mammalian Cells. Mol Ther 2016; 24(3):645-54.
36. MacLeod D T, Antony J, Martin A J, et al. Integration of a CD19 CAR into the TCR Alpha Chain Locus Streamlines Production of Allogeneic Gene-Edited CART Cells. Mol Ther 2017; 25(4): 949-961.
37. Eyquem J, Mansilla-Soto J, Giavridis T, et al. Targeting a CAR to the TRAC locus with CRISPR/Cas9 enhances tumour rejection. Nature 2017; 543(7643):113-117.
38. Provasi E, Genovese P, Lombardo A, et al. Editing T cell specificity towards leukemia by zinc finger nucleases and lentiviral gene transfer. Nat Med 2012; 18(5):807-815.
39. Long A H, Haso W M, Shern J F, et al. 4-1BB costimulation ameliorates T cell exhaustion induced by tonic signaling of chimeric antigen receptors. Nat Med 2015; 21(6):581-590.
40. Osborn M J, Webber B R, Knipping F, et al. Evaluation of TCR Gene Editing Achieved by TALENs, CRISPR/Cas9, and megaTAL Nucleases. Mol Ther. 2016; 24(3): 570-581.
41. Vakulskas C A, Dever D P, Rettig G R, et al. A high-fidelity Cas9 mutant delivered as a ribonucleoprotein complex enables efficient gene editing in human hematopoietic stem and progenitor cells. Nat Med 2018; 24(8):1216-1224.
42. Hendel A, Bak R O, Clark J T, et al. Chemically modified guide RNAs enhance CRISPR-Cas genome editing in human primary cells. Nat Biotechnol 2015; 33(9):985-989.
43. Qasim W. Allogeneic CART cell therapies for leukemia. Am J Hematol 2019; 1-5.
44. Ghosh A, Smith M, James S E, et al. Donor CD19 CAR T cells exert potent graft-versus-lymphoma activity with diminished graft-versus-host activity. Nat Med 2017; 23(2):242-249.
45. Poirot L, Philip B, Schiffer-Mannioui C, et al. Multiplex Genome-Edited T-cell Manufacturing Platform for "Off-the-Shelf" Adoptive T-cell Immunotherapies. Cancer Res 2015; 75(18):3853-3864.
46. Qasim W, Zhan H, Samarasinghe S, et al. Molecular remission of infant B-ALL after infusion of universal TALEN gene-edited CAR T cells. Sci Transl Med 2017; 9(374):eaaj2013.
47. Barrett D M, Seif A E, Carpenito C, et al. Noninvasive bioluminescent imaging of primary patient acute lymphoblastic leukemia: a strategy for preclinical modeling. Blood 2011; 118(15):e112-e117.
48. Sano H, Mochizuki K, Kobayashi S, et al. Two Occurrences of Leukemia Relapse Due to Mismatched HLA Loss After Haploidentical Stem Cell Transplantation From Different Family Donors With KIR Ligand Mismatch. J Pediatr Hematol Oncol. 2020; 42(2):e104-e106.
49. Christopher M J, Petti A A, Rettig M P, et al. Immune Escape of Relapsed AML Cells after Allogeneic Transplantation. N Engl J Med. 2018; 379(24):2330-2341.
50. Vago L, Perna S K, Zanussi M, et al. Loss of Mismatched HLA in Leukemia after Stem-Cell Transplantation. N Engl J Med. 2009; 361(5):478-488.
51. Kenderian S S, Porter D L, Gill S. Chimeric Antigen Receptor T Cells and Hematopoietic Cell Transplantation: How Not to Put the CART Before the Horse. Biol Blood Marrow Transplant 2017; 23(2):235-246.
52. Park J H, Rivière I, Gonen M, et al. Long-Term Follow-up of CD19 CAR Therapy in Acute Lymphoblastic Leukemia. N Engl J Med. 2018; 378(5):449-459.
53. Maude S L, Frey N, Shaw P A, et al. Chimeric Antigen Receptor T Cells for Sustained Remissions in Leukemia. N Engl J Med. 2014; 371(16):1507-1517.
54. Luznik L, Fuchs E J. High-dose, post-transplantation cyclophosphamide to promote grafthost tolerance after allogeneic hematopoietic stem cell transplantation. Immunol Res. 2010; 47(1-3):65-77.

55. Luznik L, Bolaños-Meade J, Zahurak M, et al. High-dose cyclophosphamide as single agent, short-course prophylaxis of graft-versus-host disease. Blood. 2010; 115 (16):3224-3230.
56. Hoffmann J-M, Schubert M-L, Wang L, et al. Differences in Expansion Potential of Naïve Chimeric Antigen Receptor T Cells from Healthy Donors and Untreated Chronic Lymphocytic Leukemia Patients. Front Immunol 2018; 8:1956.
57. Chongsathidkiet P, Jackson C, Koyama S, et al. Sequestration of T cells in bone marrow in the setting of glioblastoma and other intracranial tumors. Nat Med 2018; 24(9):1459-1468.
58. Qin H, Ishii K, Nguyen S, et al. Murine Pre-B cell ALL induces T cell dysfunction not fully reversed by introduction of a chimeric antigen receptor. Blood 2018; 132: 1899-1910.
59. Knaus H A, Berglund S, Hackl H, et al. Signatures of CD8+ T cell dysfunction in AML patients and their reversibility with response to chemotherapy. JCI Insight 2018; 3(21):e120974.
60. Dai H, Zhang W, Li X, et al. Tolerance and efficacy of autologous or donor-derived T cells expressing CD19 chimeric antigen receptors in adult B-ALL with extramedullary leukemia. Oncoimmunology. 2015; 4(11): e1027469.
61. Yang Y, Kohler M E, Chien C D, et al. TCR engagement negatively affects CD8 but not CD4 CAR T cell expansion and leukemic clearance. Sci Transl Med 2017; 9(417):eaag1209.
62. Zhao J, Song Y, Liu D. Clinical trials of dual-target CAR T cells, donor-derived CAR T cells, and universal CAR T cells for acute lymphoid leukemia. J Hematol Oncol. 2019; 12(1):17.
63. Torikai H, Reik A, Liu P-Q, et al. A foundation for universal T-cell based immunotherapy: T cells engineered to express a CD19-specific chimeric-antigen-receptor and eliminate expression of endogenous TCR. Blood 2012; 119(24):5697-5705.
64. Torikai H, Reik A, Soldner F, et al. Toward eliminating HLA class I expression to generate universal cells from allogeneic donors. Blood 2013; 122(8):1341-9.
65. Ren J, Liu X, Fang C, Jiang S, June C H, Zhao Y. Multiplex Genome Editing to Generate Universal CAR T Cells Resistant to PD1 Inhibition. Clin Cancer Res 2017; 23(9):2255-2266.
66. Gornalusse G G, Hirata R K, Funk S E, et al. HLA-E-expressing pluripotent stem cells escape allogeneic responses and lysis by NK cells. Nat Biotechnol 2017; 35(8):765-772.
67. Brudno J N, Lam N, Vanasse D, et al. Safety and feasibility of anti-CD19 CAR T cells with fully human binding domains in patients with B-cell lymphoma. Nat Med. 2020; 26(2):270-280.
68. Zhou X, Dotti G, Krance R A, et al. Inducible caspase-9 suicide gene controls adverse effects from alloreplete T cells after haploidentical stem cell transplantation. Blood 2015; 125(26):4103-13.

Example 2. Supplementary Methods

AAV Production rAAV6 was produced as previously described (1) or acquired from Vigene Biosciences Inc. The absolute concentration of ITR copy numbers was determined by Droplet Digital PCR (Bio-rad) using previously reported primer and probe sets (2).

T Cell Culture and Genome Editing

The TCRαβ+/CD19+ cell fraction (non-target fraction from the graft manipulation procedure) was used fresh or cryopreserved. Cells were cultured in X-VIVO 15 (Lonza) supplemented with 5% human AB serum (Sigma), 100 IU/ml recombinant human IL-2 (Peprotech). Medium changes were performed every 2-4 days and T cells maintained at a target density of $5 \times 10^5$ cells/ml unless otherwise indicated.

T cells were activated with Dynabeads Human T cell Activator (Gibco) for 3 days and beads removed before electroporation. For gene editing, electroporation was performed as previously described (1). HPLC-purified sgRNA with 2'-O-methyl-3'-phosphorothioate modifications at the three terminal nucleotides on both ends (3) (Synthego) was complexed with high-fidelity spCas9 protein (4) (IDT) at a molar ration of 2.5:1 (sgRNA: protein) and electroporated in buffer P3 (Lonza) into activated T cells using a 4D-Nucleofector (Lonza) in 16-cuvette strips. $1 \times 10^6$ activated T cells were used per electroporation using program EO-115. The cells were resuspended directly after electroporation in 80 μl of complete T cell medium and then diluted to the target density. For gene targeting, cells were incubated within 15 minutes after electroporation with rAAV6 for transduction at a multiplicity of infection (MOI) of >5000 vg/cell unless otherwise stated. After the specified transduction time, the suspension was diluted with complete medium to reach the target cell concentration as indicated.

In Vitro Cytokine Measurement and Cytotoxicity Assay

CD19+ Nalm6-GL cells stably expressing GFP and Firefly Luciferase (FLuc) (5) and CD19+ Raji cells, also stably expressing GFP and Firefly Luciferase, were used in co-culture assays with the CAR T cells or control T cells at different effector:target ratios for 20 hours. Concentrations of IL-2 and IFN-γ in supernatant were measured with the respective ELISA kits (Biolegend). For cytotoxicity assays, the cells were co-cultured and the absolute number of GFP+ cells in culture determined by high-throughput flow cytometry on a CytoFLEX (Beckman Coulter) after adding a specified number of CountBright Absolute Counting Beads (Thermo Fisher Scientific) to the cell suspension. The number of GFP+ cells killed were estimated relative to control samples in which target cells were cultured without effector cells with the formula $(100-((GFP^+count_{Control}-GFP^+count_{CAR-T})/GFP+count_{Control}) \times 100)$.

Off-Target Analysis

COSMID (crispr.bme.gatech.edu) (6) was used to identify potential off-target sites in the human genome (hg38) allowing up to 3 mismatches or 1 bp deletion/insertion and 1 mismatch in the 19 PAM-proximal bases.

For empirical analysis of predicted off-targets, T cells from 6 different donors were electroporated with Cas9 RNP targeting TRAC or mock electroporated and genomic DNA extracted using the Qiagen Blood and Tissue kit. Primers for amplification of all predicted sites were designed by the COSMID program. All genomic loci were amplified by specific PCR, barcoded in a second round of PCR, pooled at equimolar ratios and sequenced using an Illumina MiSeq with 250 bp paired end reads as described previously (7). The resulting data was analyzed with the script indelQuantificationFromFastqPaired-1.0.1.pl (8).

REFERENCES

1. Bak R O, Dever D P, Porteus M H. CRISPR/Cas9 genome editing in human hematopoietic stem cells. Nat Protoc 2018; 13(2):358-376.

2. Aurnhammer C, Haase M, Muether N, et al. Universal Real-Time PCR for the Detection and Quantification of Adeno-Associated Virus Serotype 2-Derived Inverted Terminal Repeat Sequences. Hum Gene Ther Methods 2012; 23(1):18-28.
3. Hendel A, Bak R O, Clark J T, et al. Chemically modified guide RNAs enhance CRISPR-Cas genome editing in human primary cells. Nat Biotechnol 2015; 33(9):985-989.
4. Vakulskas C A, Dever D P, Rettig G R, et al. A high-fidelity Cas9 mutant delivered as a ribonucleoprotein complex enables efficient gene editing in human hematopoietic stem and progenitor cells. Nat Med 2018; 24(8): 1216-1224.
5. Barrett D M, Seif A E, Carpenito C, et al. Noninvasive bioluminescent imaging of primary patient acute lymphoblastic leukemia: a strategy for preclinical modeling. Blood 2011; 118(15):e112-e117.
6. Cradick T J, Qiu P, Lee C M, Fine E J, Bao G. COSMID: A Web-based Tool for Identifying and Validating CRISPR/Cas Off-target Sites. Mol Ther—Nucleic Acids 2014; 3e214.
7. Lee C M, Cradick T J, Bao G. The *Neisseria meningitidis* CRISPR-Cas9 System Enables Specific Genome Editing in Mammalian Cells. Mol Ther 2016; 24(3):645-54.
8. Lin Y, Cradick T J, Brown M T, et al. CRISPR/Cas9 systems have off-target activity with insertions or deletions between target DNA and guide RNA sequences. Nucleic Acids Res 2014; 42(11):7473-85.

Example 3. Genome Editing of Graft-Derived T Cells for Post-Transplant Immunotherapy in Combination with TCRαβ+/CD19+-Depleted Haploidentical HSCT Background High-risk acute lymphoblastic leukemia is associated with poor outcomes if it is refractory or relapsed. αβ+ T cell/CD19+ B cell-depleted haploidentical HSCT makes a donor available for most patients, is associated with very low risk of high-grade GvHD and low non-relapse mortality (<10%). A remaining challenge is the occurrence of relapses post-HSCT.

Autologous CAR T cells are efficacious in achieving remissions in high-risk patients. A limitation is their manufacturing from patient-derived T cells, which are often impaired in numbers and function due to the malignancy and can lead to manufacturing failures.

Approach

The present approach includes the following steps: i) Development of a CAR T cell product to combine with αβ haplo-HSCT to increase antileukemic efficacy and decrease MRD; ii) Use αβ+ T cells removed during graft processing for CAR T cell manufacturing from healthy donor; iii) Knockout of the TCR to abolish alloreactivity and full compatibility with patient's new immune system after HSCT; iv) Targeted integration of the CAR by CRISPR/Cas9-based genome editing to avoid randomly integrating vectors. See, e.g., FIG. 1D.

Methods

We prospectively collected TCRαβ3+ T cells left over from the αβ+ T cell/CD19+ B cell depletion process from 9 haploidentical donors. We used genome editing with Cas9 ribonucleoprotein and AAV6 to disrupt the T cell receptor (TCR) and integrate a CD19-specific CAR into the TRAC locus. See, e.g., FIG. 2A.

Results

Genome editing of αβ+ T cells removed from the graft is highly efficient: Cas9 RNP/AAV6-mediated genome editing leads to high frequencies of TCR knockout and targeted integration of the CAR and selection marker in >65% of the cells. We consistently observed high frequencies of genome editing across cells from 9 different donors.

Depletion of residual αβ TCR+ cells: Depletion of residual T cells expressing TCR by magnetic beads using clinically-scalable reagents is highly efficient. Frequencies of residual cells are low enough to allow the administration of relevant CAR T cell doses with less that $1 \times 10^4$/kg potentially alloreactive T cells. See, e.g., FIGS. 2E-2F.

Expansion of CAR T-cells after genome editing: After an initial cell loss due to the editing procedure, the cells recover and continue to expand rapidly with only slight impairment of cell proliferation due to AAV treatment. See, e.g., FIG. 9.

Genome edited CAR T cells show antileukemic activity in vitro: During co-culture with the CD19+ lymphoblastic leukemia cell line Nalm6-GL, the CAR T cells produce IL-2 and IFN-gamma and eradicate the target cells even at low E:T ratios. See, e.g., FIGS. 3A, 10.

Genome edited CAR T cells eradicate leukemia in vivo: The CAR T cells eradicate Nalm6 cells in a xenograft model in NSG mice. $5 \times 10^6$ cells per mouse lead to persistent remission while the lower dose increased survival significantly but eventually the mice relapsed. p<0.05 for both groups compared to the controls in a log rank test. See, e.g., FIGS. 4A, 4B.

Off-target analysis by targeted next-generation sequencing: T cells from 6 donors were electroporated with RNP targeting TRAC, using high-fidelity Cas9 protein. Deep sequencing of all potential off-target sites predicted by the COSMID algorithm revealed no detectable InDel formation above the detection threshold. The graph shows the quantification of InDel frequencies at all 40 putative off-target sites after subtraction of background (determined using mock electroporated samples). See, e.g., FIG. 5B.

Conclusions

This study led to the following conclusions: i) αβ+ T cell depleted haploidentical HSCT is now a valid option for children with high-risk leukemia lacking a fully matched related donor; ii) CAR T cells are very effective in inducing remissions and have the potential to decrease relapse risk after haplo-HSCT; iii) αβ+ T cells removed from the graft for haplo-HSCT can be engineered into CAR T cells lacking allo-reactivity; and iv) the combination of haplo-HSCT and CAR T cells has several appealing features: a) the possibility to administer the CAR T cells during lymphopenia after HSCT; b) the patient's immune system after HSCT will be syngeneic to the CAR T cells and the high available cell number allows the repeated production of CAR T cells with, e.g., switch of specificities; and c) the reduction of the disease burden by previous HSCT could potentially improve CAR T cell outcomes and prevent side-effects.

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of treating leukemia in a subject that has previously received a hematopoietic stem cell transplant from an HLA-matched donor, the method comprising:
   i) introducing into a plurality of αβ T cells from the donor a guide RNA targeting the TRAC locus, an RNA-guided nuclease, and a homologous repair template comprising a polynucleotide encoding a CD19-specific chimeric antigen receptor (CAR), wherein the RNA-guided nuclease cleaves the endogenous T cell receptor antigen constant (TRAC) locus in the plurality of cells and the polynucleotide encoding the CD19-specific CAR is integrated in-frame into the cleaved TRAC locus;
   ii) expanding the modified T cells in culture to generate a population of modified CAR T cells; and
   iii) administering the modified CAR T cells to the subject.

2. The method of claim 1, wherein the hematopoietic stem cell transplant comprised hematopoietic stem and progenitor cells (HSPCs), NK cells, and γδ T cells from a graft of the donor, and wherein αβ T cells and B cells had been removed from the graft prior to the transplantation.

3. The method of claim 2, wherein the plurality of αβ T cells used in the method are αβ T cells that had been previously removed from the graft prior to the transplantation.

4. The method of claim 1, wherein the guide RNA and the RNA-guided nuclease are introduced into the cells as a ribonucleoprotein (RNP) by electroporation.

5. The method of claim 1, wherein the homologous repair template is transduced into the cells using a recombinant adeno-associated virus (rAAV) serotype 6 vector.

6. The method of claim 5, wherein the cells are present at a concentration of at least $5 \times 10^6$ cells/ml during the transduction of the rAAV serotype 6 vector.

7. The method of claim 5, wherein the multiplicity of infection (MOI) of the rAAV vector is at least 2500 vg/cell.

8. The method of claim 7, wherein the MOI is 5000 vg/cell.

9. The method of claim 1, wherein the RNA-guided nuclease is Cas9.

10. The method of claim 1, wherein the guide RNA targets exon-1 of the TRAC locus.

11. The method of claim 1, wherein the CAR further comprises a CD28 costimulatory domain.

12. The method of claim 1, wherein the introduction of the guide RNA targeting the TRAC locus, the RNA-guided nuclease, and the homologous repair template comprising the polynucleotide encoding the CD19-specific chimeric antigen receptor (CAR) into the plurality of αβ T cells results in a loss of TCR expression in and/or the presence of the CAR on the surface of at least 70%, 80%, 90%, 95%, or more of the cells.

13. The method of claim 1, further comprising a purification step wherein TCR+ cells are selectively eliminated from the population of modified CAR T cells prior to administration to the subject.

14. The method of claim 13, wherein the purification step results in a maximum of 0.05% TCR$^+$α β$^+$ cells in the population prior to administration to the subject.

15. The method of claim 1, wherein the method causes a reduction in the leukemia burden and/or does not cause graft versus host disease (GvHD) in the subject.

16. The method of claim 1, wherein the cells are administered to the subject intravenously.

17. The method of claim 1, wherein the subject is a human.

18. The method of claim 1, wherein the subject is a pediatric patient.

19. The method of claim 1, wherein the subject has relapsed or refractory B cell precursor acute lymphoblastic leukemia (r/r BCP-ALL).

\* \* \* \* \*